(12) United States Patent
Paripati et al.

(10) Patent No.: US 9,056,893 B2
(45) Date of Patent: Jun. 16, 2015

(54) METHOD AND APPARATUS FOR TREATMENT OF BIOMASS SUBSTRATES

(71) Applicants: Praveen Paripati, Reston, VA (US); Anantharam Dadi, Toledo, OH (US)

(72) Inventors: Praveen Paripati, Reston, VA (US); Anantharam Dadi, Toledo, OH (US)

(73) Assignee: Suganit Systems, Inc., Reston, VA (US)

( * ) Notice: Subject to any disclaimer, the term of this patent is extended or adjusted under 35 U.S.C. 154(b) by 0 days.

(21) Appl. No.: 13/923,455

(22) Filed: Jun. 21, 2013

(65) Prior Publication Data

US 2014/0004563 A1 Jan. 2, 2014

Related U.S. Application Data

(60) Provisional application No. 61/788,051, filed on Mar. 15, 2013, provisional application No. 61/663,315, filed on Jun. 22, 2012.

(51) Int. Cl.

| | |
|---|---|
| *C12P 19/02* | (2006.01) |
| *C12M 1/02* | (2006.01) |
| *C08B 15/08* | (2006.01) |
| *C08H 7/00* | (2011.01) |
| *D21C 3/04* | (2006.01) |
| *D21C 7/10* | (2006.01) |
| *D21C 3/26* | (2006.01) |
| *C07K 1/14* | (2006.01) |
| *C12P 19/14* | (2006.01) |
| *C07H 1/08* | (2006.01) |
| *C07G 1/00* | (2011.01) |
| *C12M 1/00* | (2006.01) |
| *C08B 15/00* | (2006.01) |
| *C08H 8/00* | (2010.01) |
| *C13K 1/02* | (2006.01) |

(52) U.S. Cl.
CPC ............... *C07K 1/145* (2013.01); *C12P 19/14* (2013.01); *C07H 1/08* (2013.01); *C07G 1/00* (2013.01); *Y02E 50/343* (2013.01); *C12M 45/00* (2013.01); *C12P 2201/00* (2013.01); *Y02E 50/10* (2013.01); *Y02E 50/16* (2013.01); *Y02E 50/13* (2013.01); *C08B 15/00* (2013.01); *C08H 6/00* (2013.01); *C08H 8/00* (2013.01); *C12P 19/02* (2013.01); *C12M 45/03* (2013.01); *C12M 45/06* (2013.01); *C12M 45/07* (2013.01); *C13K 1/02* (2013.01); *C12P 2203/00* (2013.01)

(58) Field of Classification Search
CPC ............... C08L 1/02; C08L 1/08; C10G 3/40; C10G 3/00; C10G 32/02; C10G 2300/10; C10G 2300/1011; C10G 2300/1014; D21C 1/06; D21C 1/00; D21C 3/02; D21C 5/005; C12N 13/00; B01J 2219/0854; B01J 19/08; B01J 19/12; B01J 19/126; B01J 19/129; H05B 6/00; H05B 6/46; H05B 6/50; H05B 6/64

See application file for complete search history.

(56) References Cited

U.S. PATENT DOCUMENTS

| | | | |
|---|---|---|---|
| 5,143,626 A | 9/1992 | Nugent | |
| 5,599,345 A * | 2/1997 | Edwards et al. | 606/41 |
| 5,624,530 A | 4/1997 | Sadykhov et al. | |
| 6,824,599 B2 | 11/2004 | Swatloski et al. | |
| 7,674,608 B2 | 3/2010 | Varanasi et al. | |
| 8,030,030 B2 | 10/2011 | Varanasi et al. | |
| 8,173,406 B1 | 5/2012 | Wang et al. | |
| 2008/0026431 A1 | 1/2008 | Saito et al. | |
| 2008/0190013 A1 | 8/2008 | Argyropoulos | |
| 2008/0227162 A1 | 9/2008 | Varanasi et al. | |
| 2010/0087687 A1 | 4/2010 | Medoff | |
| 2010/0269990 A1 | 10/2010 | Dottori et al. | |
| 2010/0287826 A1 * | 11/2010 | Hoffman et al. | 44/605 |
| 2010/0304440 A1 | 12/2010 | Medoff | |
| 2011/0144359 A1 | 6/2011 | Heide et al. | |
| 2011/0251377 A1 | 10/2011 | Rahman et al. | |
| 2011/0256615 A1 * | 10/2011 | Brady et al. | 435/267 |
| 2011/0287498 A1 * | 11/2011 | Medoff et al. | 435/135 |
| 2012/0324785 A1 * | 12/2012 | Taylor et al. | 44/577 |
| 2013/0011895 A1 | 1/2013 | Medoff et al. | |

FOREIGN PATENT DOCUMENTS

| | | |
|---|---|---|
| CA | 2 674 534 | 7/2008 |
| WO | WO 2005/017252 | 2/2005 |
| WO | WO 2008/090156 | 7/2008 |

(Continued)

OTHER PUBLICATIONS

Tadesse, H. et al. 2011. Advances on biomass pretreatment using ionic liquids: An overview. Energy & Environmental Science 4:3913-3929. specif. pp. 3922.*

(Continued)

*Primary Examiner* — John S Brusca
*Assistant Examiner* — Sharon M Papciak
(74) *Attorney, Agent, or Firm* — Hunton & Williams LLP

(57) ABSTRACT

A system and method for the treatment of biomass comprising mixing a biomass with an ionic liquid (IL) to swell the biomass and electromagnetic (EM) heating, preferably radiofrequency (RF) heating, said biomass. Additionally, a method of acidolysis of biomass comprising mixing biomass in an ionic liquid (IL) to swell the biomass; adding an acid, to lower the pH of the biomass below pH 7; applying radio frequency (RF) heating to the biomass to heat to a target temperature range; applying ultrasonic heating, electromagnetic (EM) heating, convective heating, conductive heating, or combinations thereof, to the biomass to maintain the biomass at a target temperature range; washing the treated biomass; and recovering sugars and released lignin.

45 Claims, 11 Drawing Sheets

(56) References Cited

FOREIGN PATENT DOCUMENTS

| WO | WO 2012/064868 | 5/2012 |
|----|----------------|--------|
| WO | WO 2013/000074 | 1/2013 |

OTHER PUBLICATIONS

Britannica Online Encyclopedia—EM radiation (Electromagnetic Radiation. Datasheet [online]. Encyclopedia Britannica, Inc. Copyright 2014) [retrieved on Feb. 20, 2014]. Retrieved from the Internet: <URL: http://www.britannica.com/EBchecked/topic/183228/ electromagnetic-radiation/59182/Microwaves>. pp. 1-9. specif. pp. 1 and 3.*
Zhang, Z. et al. 2010. Microwave-assisted conversion of lignocellulosic biomass into furans in ionic liquid. Bioresource Technology 101:1111-1114. specif. pp. 1111-1113.*
Britannica Online Encyclopedia—Radio-frequency heating (Radio-frequency heating. Datasheet [online]. Encyclopedia Britannica, Inc. Copyright 2014) [retrieved on Feb. 22, 2014]. Retrieved from the Internet: <URL: http://www.britannica.com/EBchecked/topic/488902/ radio-frequency heating>. p. 1.*
Radio-frequency and Microwave Radiation. Radio-Frequency & Microwave Radiation..American Industrial Hygiene Assoc. (publisher). Third edition. Copyright 2004 American Industrial Hygiene Assoc..Author: Hitchcock, R. Timothy. Fairfax, VA. p. 1.*
Dictionary of Chemical Engineering. Solvent.Oxford University Press (publisher). First edition. Copyright 2014 Oxford University Press. Ed.: Carl Schaschke. Editorial Offices, Oxford, UK. p. 351.*
Hu, Z. et al. 2008. Alkali (NaOH) pretreatment of switchgrass by radio frequency-based dielectric heating. Applied Biochemisty and Biotechnology 148: 71-81. specif. pp. 71-75.*
Tabil, L. et al. 2011. Biomass Feedstock Pre-Processing—Part 1: Pre-Treatment. In: Biofuel's Engineering Process Technology. Chapter 18. InTech (publisher). Published online Aug. 1, 2011.Ed.: Dr. Marco Aurelio Dos Santos Bernardes, InTech Europe, Rijeka, Croatia, pp. 411-438. specif. pp. 411, 420-422.*
Dadi, et al. (2006) *Biotechnol. and Bioeng.* 95(5): 904-910.
Dadi, et al. *Applied Biochem. and Biotech.*, 2007, 136-140: 407-421.
Binder & Raines, PNAS, 2010, 107(10): 4516-4521.
Binder & Raines, J. Am. Chem. Soc., 2009, 131: 1979-1985.
Brennan et al., Recovery of Sugars from Ionic Liquid Biomass Liquor by Solvent Extraction, Bioenergy Research, 2010, 3(2): 123-133.
Brodeur, et al., Enzyme Research Article ID 787532, 2011, 17 pages.
Corma, et al., Chemical Routes for the Transformation of Biomass into Chemicals, Chem. Rev., 2007, 107: 2411-2502.
Fort, et al., Green. Chem, 2007, 9:63.
Ishikawa & Saka, Chemical Conversion of Cellulose as treated in supercritical methanol, Cellulose, 2001, 8(3): 189-195.

Jeffries "8. Biodegradation of lignin and hemicelluloses." *Biochemistry of Microbial Degradation* pp. 233-277, 1994?
Jeffries & Jin, Appl Microbiol Biotechnol, 2004, 63(5): 495-509.
Kobayashi, et al., Catal. Sci. Technol., 2012, 2: 869-883.
Li, et al., Ind. Eng. Chem. Res., 2010, 49(7): 3126-3136.
Long, et al., Green Chem, 2011, 13: 2334-2338.
Lynd, Annu Rev Energy Environ, 1996, 21: 403-465.
Marra, et al., Journal of Food Engineering, 2009, 91(4): 497-508.
Murugesan & Linhardt, Current Organic Synthesis, 2005, 2: 437-451.
Peng, et al., Molecules, 2010, 15: 5258-5272.
Robinson, A Mild, Chemical Conversion of Cellulose to Hexane and Other Liquid Hydrocarbon Fuels and Additives, ACS Fuel Chemistry Preprints, 1995, 40(3): 729.
Sheldon, Chem.Commun, 2001, 23: 2399-2407.
Singh et al., Optimisation of downstream processing parameters for the recovery of pectinase from the fermented bran of *Aspergillus carbonarius*, Process Biochem, 1999, 35:411-417.
Tao, et al., Catalytic Conversion of cellulose to chemicals in ionic liquid, 2011, Carbohydrate Research 346(1): 58-63.
Viamajala, et al. Heat and Mass Transport in Processing of Lignocellulosic Biomass for Fuels and Chemicals, in Sustainable Biotechnology. Sources of Renewable Energy, O.V. Singh and S.P. Harvey, Editors. 2010, Springer: London, New York [Table of Contents].
Wang, et al., Journal of Food Science, 2003, 68(2): 539-544.
Wyman, et al., Bioresource Technology, 2005, 96: 1959-1966).
Zhao, et al., Science, 2007, 316(5831): 1597-1600.
International Search Report for International Patent Application No. PCT/US2013/047149, mailed Nov. 8, 2013.
NASA's Imagine the Universe! Website "Regions of the Electromagnetic Spectrum" (downloaded Jun. 25, 2014).
UCLA's ePhysics website "The Electromagnetic Spectrum" (downloaded Jun. 25, 2014).
Definition of "Non Solvent" from Dictionary.com (2014).
Ullmann's Encyclopedia of Industrial Chemistry—Section 205—Solvents, Latent Solvents and Non-Solvents, p. 626.
Wang, et al. "Ionic Liquid Processing of Cellulose." *Chemical Society Reviews*, 2012, 41: 1519-1537.
International Search Report for International Patent Application No. PCT/IS2013/047149 mailed Nov. 8, 2013.
Written Opinion for International Patent Application No. PCT/US2013/047149 mailed Nov. 8, 2013.
International Search Report for International Patent Application No. PCT/US2014/029063 (Jul. 28, 2014).
Written Opinion for International Patent Application No. PCT/US2014/029063 (Jul. 28, 2014).
Sheldon (2001) *Chem.Commun.* 23: 2399-2407.
Earle & Seddon (2000) *Pure Appl. Chem.* 72(7): 1391-1398.
Wasserscheid & Keim (2000) *Angew. Chem. Int. Ed.* 39: 3772-3789.
Singh, et al. *Process Biochemistry* (1999) 35: 411-417.

* cited by examiner

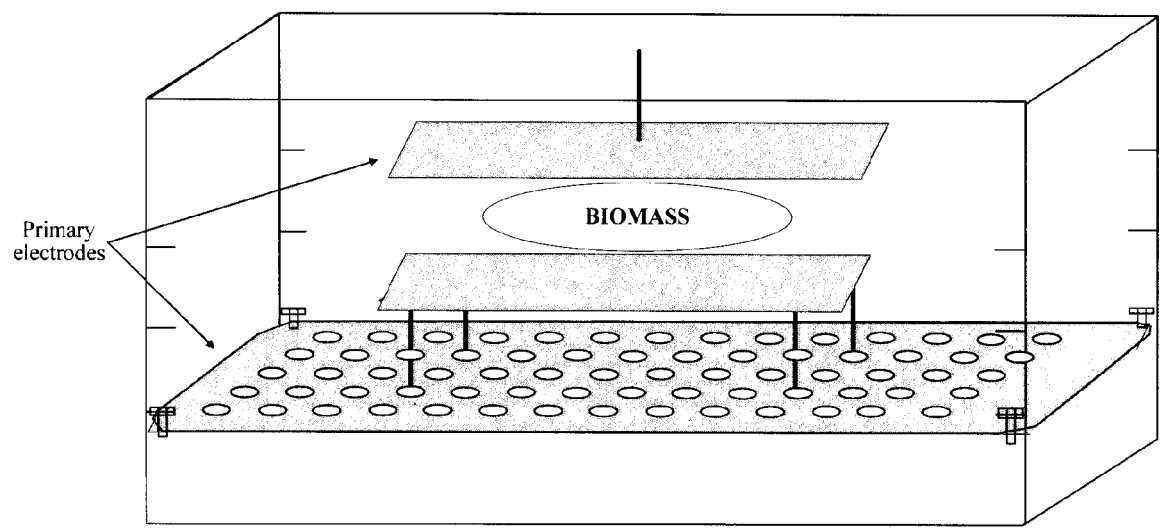
FIG. 2a is a schematic diagram of an EM oven interior showing electrode positions

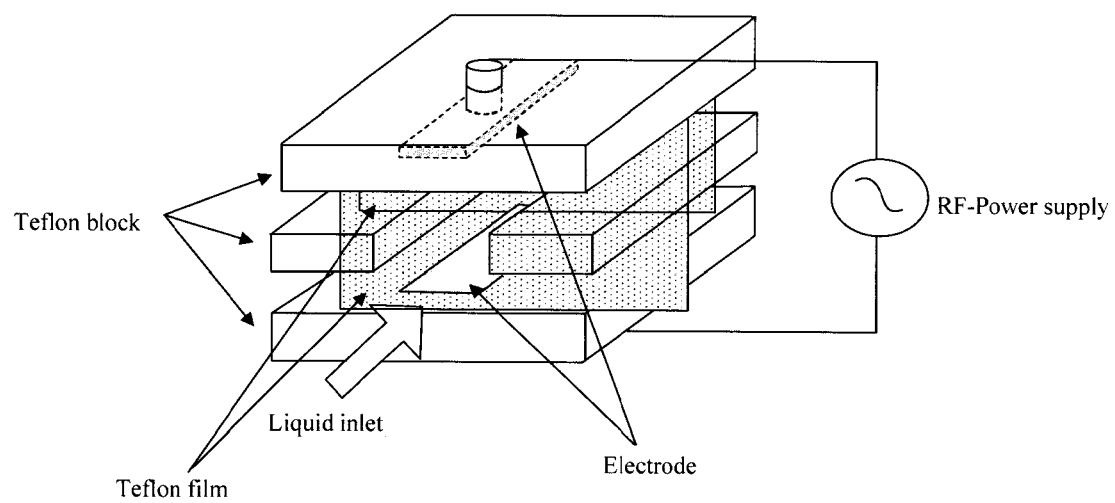
FIG. 2b is a schematic diagram of a dielectric radiofrequency system.

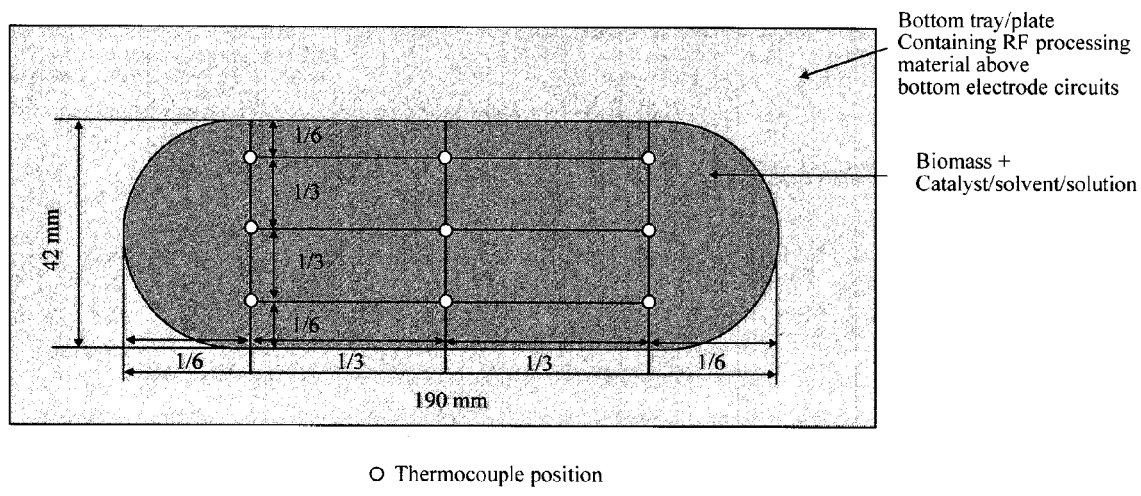
FIG. 2c is a schematic side profile of thermocouple/fiber optic jig for temperature measurement during EM wave processing of biomass.

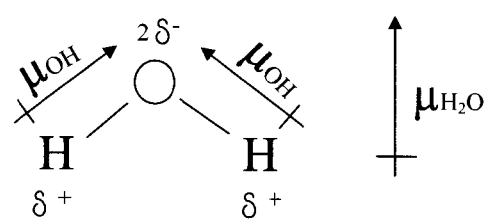
FIG. 3 Electronic configuration of a water molecule and (b) dipole reorientation in an electric field

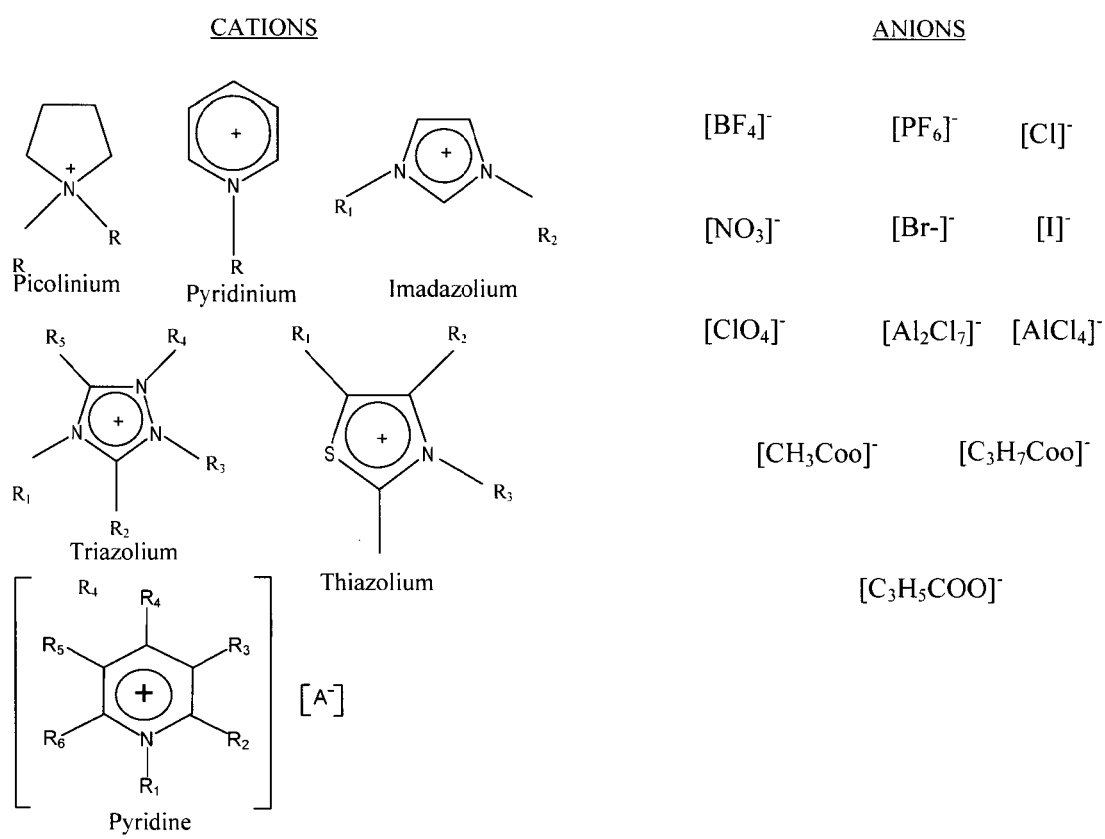
FIG. 4 Exemplary cation and anion components of ionic liquids

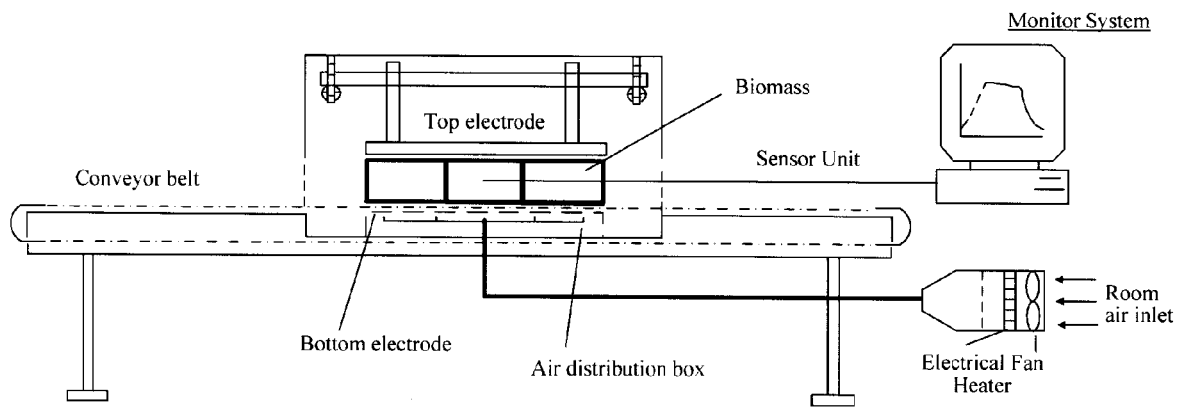
FIG. 5a is a schematic diagram of a continuous belt press radiofrequency apparatus of biomass processing

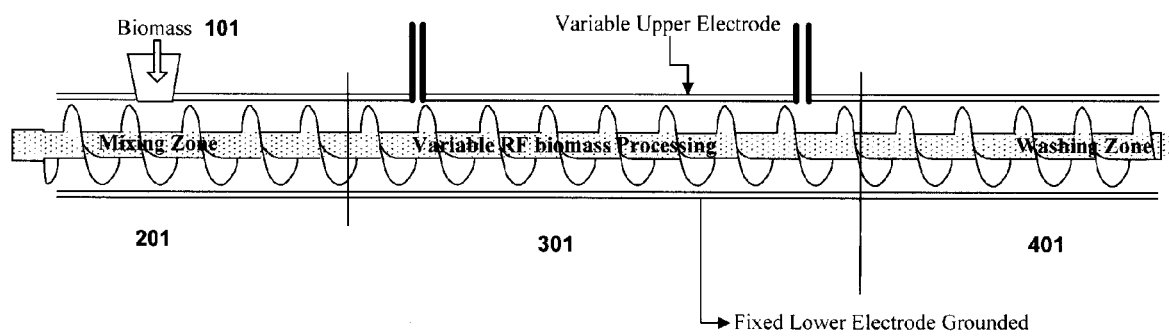
FIG. 5b is a schematic diagram of a lignocellulosic biomass processing in a radiofrequency treating system.

METHOD AND APPARATUS FOR TREATMENT OF BIOMASS SUBSTRATES

CROSS REFERENCE

This patent application claims priority to U.S. Provisional Patent Application No. 61/788,052, filed Mar. 15, 2013, and U.S. Provisional Application No. 61/663,315, filed Jun. 22, 2012, both of which are herein incorporated by reference in their entirety.

FIELD OF THE INVENTION

The present invention relates to the processing of biomass or its components comprising mixing the biomass an with ionic liquid (IL) and treating the mixture with electromagnetic energy (EM) (e.g., radiofrequency (RF)) heating for conversion to renewable fuels, chemicals, materials, renewable fuels, ethanol, butanol, lactic acid, gasoline, biodiesel, jet fuel, methane, hydrogen, plastics, composites, protein, drugs, fertilizers, and other value added products. The invention relates to methods and systems for treating biomass/ionic liquid (IL) slurries, solutions and suspensions utilizing electromagnetic energy (EM) heating, optionally in combination with acids (acidolysis), for effective and amenable conversion of the biomass and derived products to renewable fuels, chemicals, materials, renewable fuels, ethanol, butanol, lactic acid, gasoline, biodiesel, jet fuel, methane, hydrogen, plastics, composites, protein, drugs, fertilizers, and other value added products, as well as the production of electricity. The invention also relates to the use of electromagnetic energy (EM) (e.g., radiofrequency (RF)) heating to dehydrate ionic liquids. The invention also relates to bioreactors comprising a reactor vessel coupled to a sensor network and a feedback system for controlling the time, temperature, pressure, and IL saturation.

BACKGROUND OF THE INVENTION

Research has been undertaken to convert biomass into transportation fuels over the past three decades. A main objective of research done during the 1990s was to develop enzymes that could hydrolyze cellulose into sugars. This enzymatic hydrolysis of pure cellulose is a slow but well established process. However, biomass does not yield pure cellulose efficiently. Some form of pretreatment is required to make the biomass amenable to efficient enzymatic hydrolysis. Although pretreatment technologies exist, none is suitable for economic production of fuels and chemicals from biomass. Brodeur, et al. (2011) *Enzyme Research* Article ID 787532, 17 pages.

Lignocellulose is the major structural component of plants and comprises cellulose, hemicellulose, and lignin. In lignocellulosic biomass, crystalline cellulose fibrils are embedded in a less well-organized hemicellulose matrix which, in turn, is surrounded by an outer lignin seal. Lignocellulosic biomass is an attractive feed-stock because it is an abundant, domestic, renewable source that can be converted to liquid transportation fuels, chemicals and polymers. The major constituents of lignocellulose are: (1) hemicellulose (20-30%), an amorphous polymer of five and six carbon sugars; (2) lignin (5-30%), a highly cross-linked polymer of phenolic compounds; and (3) cellulose (30-40%), a highly crystalline polymer of cellobiose (a glucose dimer). Cellulose and hemicellulose, when hydrolyzed into their monomeric sugars, can be converted into ethanol fuel through well established fermentation technologies. These sugars also form the feedstocks for production of a variety of chemicals and polymers. The lignin may also be recovered for use in the production of a variety of chemicals or used a fuel. The complex structure of biomass requires proper treatment to enable efficient hydrolysis (e.g., saccharification) of cellulose and hemicellulose components into their constituent sugars. Current treatment approaches suffer from slow reaction rates of cellulose hydrolysis (e.g., using the enzyme cellulase) and low sugar yields. Wyman, et al. (2005) *Bioresource Technology* 96: 1959-1966).

Contacting lingocellulosic biomass with hydrolyzing enzymes generally results in cellulose hydrolysis yields that are less than 20% of predicted results. Hence, some "pretreatment" of the biomass is invariably carried out prior to attempting the enzymatic hydrolysis of the cellulose and hemicellulose in the biomass. Pretreatment refers to a process that converts lignocellulosic biomass from its native form, in which it is recalcitrant to cellulase enzyme systems, into a form for which cellulose hydrolysis is effective. Compared to untreated biomass, effectively pretreated lignocellulosic materials are characterized by an increased surface area (porosity) accessible to cellulase enzymes, and solubilization or redistribution of lignin. Increased porosity results mainly from a combination of disruption of cellulose crystallinity, hemicellulose disruption/solubilization, and lignin redistribution and/or solubilization. The relative effectiveness in accomplishing at least some of these factors differs greatly among different existing pretreatment processes. These include dilute acid, steam explosion, hydrothermal processes, "organosolv" processes involving organic solvents in an aqueous medium, ammonia fiber explosion (AFEX), strong alkali processes using a base (e.g., ammonia, NaOH or lime), and highly-concentrated phosphoric acid treatment. Many of these methods do not disrupt cellulose crystallinity, an attribute vital to achieving rapid cellulose digestibility. Also, some of these methods are not amenable for efficient recovery of the chemicals employed in the pretreatment.

Ionic liquid pretreatment technique is effective in disrupting the recalcitrance of biomass for subsequent conversion to value added products. Anantharam, et al. (2006) "Enhancement of cellulose saccharification kinetics using an ionic liquid pretreatment step." *Biotechnol. and Bioengg.* 95(5): 904-910; Anantharam, et al. (2007) "Mitigation of cellulose recalcitrance to Enzymatic hydrolysis by ionic liquid pretreatment." *Applied Biotechnol. and Bioengg* 136-140: 407-421; Wang, et al. (2012) "Ionic Liquid Processing of Cellulose." *Chemical Society Reviews* 41: 1519-1537; U.S. Pat. No. 7,674,608; and U.S. Pat. No. 8,030,030.

For commercial viability, the pretreatment of biomass should be conducted at high solids loadings (>20% w/w) to minimize the reactor size and process utility costs. However, the non-conducting/insulating characteristics pose significant heat and mass transfer limitations when process heating is done through jacketed tanks or other heated surfaces. Therefore, in these processes, at feed concentrations >20% (w/w), heat cannot penetrate uniformly and the slurries become thick, viscous, and non-uniformly wet. Viamajala, et al. *Heat and Mass Transport in Processing of Lignocellulosic Biomass for Fuels and Chemicals, in Sustainable Biootechnology. Sources of Renewable Energy*, O. V. Singh and S. P. Harvey, Editors. 2010, Springer: London, N.Y. This poses operational challenges in overcoming any localized heating zones or large heat gradients in the reactor, resulting in ineffective treatment of the feedstock.

Therefore, there is a need in the art for a method and system of treating biomass (e.g., lignocellulosic biomass) to prepare it for hydrolysis at high solids loadings and large scale to minimize reactor size and utility costs.

SUMMARY OF THE INVENTION

This invention provides for a method for the treatment of biomass comprising mixing a biomass with an ionic liquid (IL) to swell the biomass and electromagnetic (EM) heating, preferably radiofrequency (RF) heating, said biomass.

This invention provides for a method for the treatment of biomass comprising mixing a biomass with an ionic liquid (IL) to form a biomass/IL slurry and electromagnetic (EM) heating, preferably radiofrequency (RF) heating, said biomass/IL slurry.

In another embodiment, a method for disruption of the structure of a lignocellulosic biomass may comprise incubating a biomass in an ionic liquid (IL) and applying radiofrequency (RF) heating and ultrasonics, electromagnetic (EM), convective, conductive heating, or combinations thereof.

In another embodiment, a method for conversion of the carbohydrates of biomass to sugars may comprise: mixing biomass in an ionic liquid (IL) to form a biomass/IL slurry; applying radio frequency (RF) heating to the biomass/IL slurry to heat to a target temperature range, optionally 50-220° C.; applying ultrasonics, electromagnetic (EM), convective, conductive heating, or combinations thereof, to the biomass/IL slurry to maintain the slurry at said target temperature range; washing the treated biomass; hydrolyzing the treated biomass to yield sugars, optionally pentose and hexose sugars, and release proteins and lignin.

In another embodiment, a method for conversion of the carbohydrates of biomass to sugars may comprise: mixing biomass in an ionic liquid (IL) to swell the biomass; applying radio frequency (RF) heating to the biomass to heat to a target temperature range, optionally 50-220° C.; applying ultrasonics, electromagnetic (EM), convective, conductive heating, or combinations thereof, to the biomass to maintain the biomass at said target temperature range; washing the treated biomass; hydrolyzing the treated biomass to yield sugars, optionally pentose and hexose sugars, and release lignin.

In another embodiment, a method for the conversion of cellulose to sugar may comprise mixing biomass in an ionic liquid (IL) to form a biomass/IL slurry; applying radio frequency (RF) heating to the biomass/IL slurry to heat to a target temperature range, optionally 50-220° C.; applying ultrasonics, electromagnetic (EM), convective, conductive heating, or combinations thereof, to the biomass/IL slurry to maintain the slurry at said target temperature range; precipitating amorphous cellulose and/or cellulose of reduced crystallinity by admixture with an anti-solvent; and adding cellulase to the cellulose precipitate under conditions which promote the hydrolysis of cellulose to sugars.

In another embodiment, a method for treatment of biomass may comprise incubating a biomass in a sufficient amount of an ionic liquid (IL) for a sufficient time and temperature to swell the biomass, optionally without dissolution of the biomass in the IL; applying radio frequency (RF) heating to the biomass/IL slurry to heat to a target temperature range, optionally 50-220° C.; applying ultrasonic heating to the biomass/IL slurry to maintain the slurry at said target temperature range; washing the treated biomass with a liquid non-solvent for cellulose that is miscible with water and the IL; and contacting said washed treated biomass with an aqueous buffer comprising enzymes capable of hydrolyzing cellulose and hemicellulose to produce sugars, optionally hexose and pentose sugars.

In a further embodiment, a method of acidolysis of biomass may comprise mixing biomass in an ionic liquid (IL) to form a biomass/IL slurry; adding an acid, optionally sulfuric acid, hydrochloric acid, nitric acid, or phosphoric acid, optionally lowering the pH of the slurry below pH 7, optionally a pH between 1-6; applying radio frequency (RF) heating to the biomass/IL slurry to heat to a target temperature range, optionally 50-220° C.; applying ultrasonic heating, electromagnetic (EM) heating, convective heating, conductive heating, or combinations thereof, to the biomass/IL slurry to maintain the slurry at said target temperature range; optionally washing the treated biomass; and recovering sugars, optionally pentose and hexose sugars, and released proteins and lignin.

In another embodiment, a method for the conversion of cellulose to sugar may comprise mixing biomass in an ionic liquid (IL) to swell the biomass; applying radio frequency (RF) heating to the biomass to heat to a target temperature range, optionally 50-220° C.; applying ultrasonics, electromagnetic (EM), convective, conductive heating, or combinations thereof, to the biomass to maintain the biomass at said target temperature range; precipitating amorphous cellulose and/or cellulose of reduced crystallinity by admixture with an anti-solvent; and adding cellulase to the cellulose precipitate under conditions which promote the hydrolysis of cellulose to sugars.

In another embodiment, a method for treatment of biomass may comprise incubating a biomass in a sufficient amount of an ionic liquid (IL) for a sufficient time and temperature to swell the biomass without dissolution of the biomass in the IL; applying radio frequency (RF) heating to the IL swelled biomass to heat to a target temperature range, optionally 50-220° C.; applying ultrasonic heating to the IL swelled biomass to maintain the IL swelled biomass at said target temperature range; washing the treated biomass with a liquid non-solvent for cellulose that is miscible with water and the IL; and contacting said washed treated biomass with an aqueous buffer comprising enzymes capable of hydrolyzing cellulose and hemicellulose to produce sugars, optionally hexose and pentose sugars.

In a further embodiment, a method of acidolysis of biomass may comprise mixing biomass in an ionic liquid (IL) to swell but not dissolve the biomass; adding an acid, optionally sulfuric acid, hydrochloric acid, nitric acid, or phosphoric acid, optionally lowering the pH of the biomass below pH 7, optionally a pH between 1-6; applying radio frequency (RF) heating to the IL swelled biomass to heat to a target temperature range, optionally 50-220° C.; applying ultrasonic heating, electromagnetic (EM) heating, convective heating, conductive heating, or combinations thereof, to the IL swelled biomass to maintain the biomass at said target temperature range; optionally washing the treated biomass; and recovering sugars, optionally pentose and hexose sugars, and released proteins and lignin.

In another embodiment, the method may further comprise the addition of a base, optionally NaOH or KOH to neutralize the pH of the biomass/IL slurry.

In another embodiment, the method may further comprise the addition of a base, optionally NaOH or KOH to neutralize the pH of the IL swelled biomass.

In another embodiment, the pH may be about 1, 2, 3, 3.5, 4, 4.5, 5, 5.5, 5.8, 6, 6.5, or 6.8, 1-3, 2-4, 3-5, 2-6, 3.5-4.5, or 4-6.

In another embodiment, the biomass may be agricultural residues, optionally corn stover, wheat straw, bagasse, rice hulls, or rice straw; wood and forest residues, optionally pine, poplar, douglas fir, oak, saw dust, paper/pulp waste, or wood fiber; algae, optionally red algae; kudzu; coal; cellulose, lignin, herbaceous energy crops, optionally switchgrass, reed canary grass, or miscanthus; lingocellulosic biomass, optionally comprising lignin, cellulose, and hemicellulose; plant biomass; or mixtures thereof.

In a further embodiment, the heating may comprise at least two phases, a first phase comprising application of electromagnetic (EM) heating, optionally a variable frequency in the electromagnetic spectrum, variable frequency heating, radiofrequency (RF) heating, or a combination thereof, and a second phase comprising application of ultrasonics, electromagnetic (EM), convective, conductive heating, or combinations thereof.

In a further embodiment, the application of radiofrequency heating may be for about at least 5-10 seconds, 1-30 minutes, 5-30 minutes, or 20-240 minutes.

In a further embodiment, the application of ultrasonics, electromagnetic (EM), convective, conductive heating, or combinations thereof, may be for about at least 3-30 minutes, 5-30 minutes, or 3-4 hours.

In another embodiment, the method may further comprise washing the treated biomass. In yet another embodiment, the washing may comprise washing the biomass with a liquid non-solvent for cellulose that is miscible with water and the ionic liquid (IL). In another embodiment, the liquid non-solvent used for washing may be water, an alcohol, acetonitrile or a solvent which dissolves the IL. In yet another embodiment, the wash may be recovered and treated with RF heating to dehydrate the ionic liquid.

In yet another embodiment, the ionic liquid (IL) may be 1-n-butyl-3-methylimidazolium chloride, 1-allyl-3-methyl imidazolium chloride, 3-methyl-N-butylpyridinium chloride, 1-ethyl-3-methyl imidazolium acetate, 1-ethyl-3-methyl imidazolium propionatem, or combinations thereof.

In one embodiment, a method for processing biomass may comprise mixing with ionic liquid, heating by radio frequency, optionally repeated, washing the biomass, optionally recovering the IL, hydrolysis (e.g., addition of cellulase and hemicellulases) of the cellulose and hemicellulose to their constituent monomeric sugars (e.g., five and six carbon sugars), optionally recovery of the added enzymes, separation of the hydrolystate stream comprising sugars for further processing to produce chemicals or biofuels and the residual solids comprising proteins and lignin for further processing to produce chemicals or biofuels. The ionic liquid and enzymes may be reclaimed and reused. In a further embodiment, the biomass mixture may be heated to at least about 100° C., 105° C., 110° C., 120° C., 130° C., 140° C., 150° C., or between about 130-150° C. In a further embodiment, the biomass mixture may be heated for at least about 10, 20, 30, 40, 50, 60, 120, or 180 minutes. In a further embodiment, the biomass mixture may be heated for at least about 5-30 minutes.

In one embodiment, a method for processing biomass may comprise mixing with ionic liquid, heating by radio frequency irradiation to reach a target temperature range, optionally repeated, maintaining the temperature of the biomass using of ultrasonics (e.g., sound waves with high frequency about between 15 kHz to 40 kHz, or 20 kHz and low amplitude about between 0.0001-0.025 mm), EM, convective, conductive heating, or combinations thereof, optionally repeated, washing the biomass, optionally recovering the IL and dehydrating the IL by application of radiofrequency heating, hydrolysis (e.g., addition of celluase and hemicellulases) of the cellulose and hemicellulose to their constituent monomeric sugars (e.g., five and six carbon sugars), optionally recovery of the added enzymes, separation of the hydrolystate stream comprising sugars for further processing to produce chemicals or biofuels and the residual solids comprising proteins and lignin for further processing to produce chemicals or biofuels. The enzymes may be reclaimed and reused. In a further embodiment, the biomass mixture may be heated to at least about 130° C., 140° C., 150° C., or between about 130-150° C. In a further embodiment, the biomass mixture may be heated for at least about 10, 20, 30, 40, 50, 60, 120, or 180 minutes.

In one embodiment, a method for processing biomass may comprise mixing with ionic liquid, heating by radio frequency irradiation to reach a target temperature range, optionally repeated, maintaining the temperature of the biomass using of ultrasonics (e.g., sound waves with high frequency about between 15 kHz to 40 kHz, or 20 kHz and low amplitude about between 0.0001-0.025 mm), EM, convective, conductive heating, or combinations thereof, optionally repeated, washing the biomass, optionally recovering the IL and dehydrating the IL by application of radiofrequency heating, hydrolysis (e.g., addition of celluase and hemicellulases) of the cellulose and hemicellulose to their constituent monomeric sugars (e.g., five and six carbon sugars), optionally recovery of the added enzymes, separation of the hydrolystate stream comprising sugars for further processing to produce chemicals or biofuels and the residual solids comprising proteins and lignin for further processing to produce chemicals or biofuels. The enzymes may be reclaimed and reused. In a further embodiment, the biomass mixture may be heated to at least about 130° C., 140° C., 150° C., or between about 130-150° C. In a further embodiment, the biomass mixture may be heated for at least about 10, 20, 30, 40, 50, 60, 120, or 180 minutes.

In another embodiment, a method for processing biomass may comprise mixing with ionic liquid, dissolving the biomass in the ionic liquid, heating by radio frequency, optionally repeated, regenerating the biomass using an antisolvent, optionally water, ethanol, methanol, acetone, or mixtures thereof, optionally recovering the IL, optionally washing the biomass, recovery of the biomass, hydrolysis (e.g., addition of cellulase and hemicellulases) of the cellulose and hemicellulose to their constituent monomeric sugars (e.g., five and six carbon sugars), optionally recovery of the added enzymes, separation of the hydrolystate stream comprising sugars for further processing to produce chemicals or biofuels and the residual solids comprising proteins and lignin for further processing to produce chemicals or biofuels. The ionic liquid and enzymes may be reclaimed and reused. In a further embodiment, the biomass mixture may be heated to at least about 130° C., 140° C., 150° C., or between about 130-150° C. In a further embodiment, the biomass mixture may be heated for at least about 10, 20, 30, 40, 50, 60, 120, or 180 minutes, optionally about 5-30 minutes.

In another embodiment, a method for processing biomass may comprise mixing with ionic liquid, dissolving the biomass in the ionic liquid, heating by radio frequency irradiation to reach a target temperature range, optionally repeated, maintaining the temperature of the mixture using of ultrasonics (e.g., sound waves with high frequency about between 15 kHz to 40 kHz, or kHz and low amplitude about between 0.0001-0.025 mm), electromagnetic irradiation (EM) (e.g., radiofrequency), convective, conductive heating, or combinations thereof, optionally repeated, regeneration of the biomass by addition of antisolvents, optionally water, ethanol, methanol, acetone, or mixtures thereof, optionally washing the regenerated biomass, optionally recovering the IL and dehydrating the IL by application of radiofrequency heating, hydrolysis (e.g., addition of celluase and hemicellulases) of the cellulose and hemicellulose to their constituent monomeric sugars (e.g., five and six carbon sugars), optionally recovery of the added enzymes, separation of the hydrolystate stream comprising sugars for further processing to produce chemicals or biofuels and the residual solids comprising proteins and lignin for further processing to produce chemicals or biofuels. The enzymes may be reclaimed and reused. In a further embodiment, the biomass mixture may be heated to at least about 130° C., 140° C., 150° C., or between about 130-150° C. In a further embodiment, the biomass mixture may be heated for at least about 10, 20, 30, 40, 50, 60, 120, or 180 minutes, optionally about 5-30 minutes.

In one embodiment, the invention provides for a method for the treatment of biomass comprising mixing a biomass with an ionic liquid (IL) to form a biomass/IL slurry and electromagnetic heating, optionally employing a variable frequency in the electromagnetic spectrum, optionally radiofrequency heating, optionally variable frequency heating, said biomass/IL slurry. In one embodiment, the biomass may be agricultural residues, optionally corn stover, wheat straw, bagasse, rice hulls, or rice straw; wood and forest residues, optionally pine, poplar, douglas fir, oak, saw dust, paper/pulp waste, or wood fiber; algae, optionally red algae; kudzu; coal; cellulose, lignin, herbaceous energy crops, optionally switchgrass, reed canary grass, or miscanthus; lingocellulosic biomass, optionally may comprise lignin, cellulose, and hemicellulose; plant biomass, or mixtures thereof.

In one embodiment, the invention provides for a method for the treatment of biomass comprising mixing a biomass with an ionic liquid (IL) to swell the biomass without dissolving the biomass in the IL and electromagnetic heating, optionally employing a variable frequency in the electromagnetic spectrum, optionally radiofrequency heating, optionally variable frequency heating, said biomass. In one embodiment, the biomass may be agricultural residues, optionally corn stover, wheat straw, bagasse, rice hulls, or rice straw; wood and forest residues, optionally pine, poplar, douglas fir, oak, saw dust, paper/pulp waste, or wood fiber; algae, optionally red algae; kudzu; coal; cellulose, lignin, herbaceous energy crops, optionally switchgrass, reed canary grass, or miscanthus; lingocellulosic biomass, optionally may comprise lignin, cellulose, and hemicellulose; plant biomass, or mixtures thereof.

In another embodiment, the heating may comprise at least two phases, a first phase may comprise application of radiofrequency (RF) heating and a second phase may comprise application of ultrasonics, electromagnetic (EM), convective, conductive heating, or combinations thereof. In another embodiment, the application of radiofrequency heating may be for about at least 5-10 seconds, 1-30 minutes, 5-30 minutes, or 20-240 minutes. In another embodiment, the application of ultrasonics, electromagnetic (EM), convective, conductive heating, or combinations thereof may be for about at least 3-30 minutes, 5-30 minutes, or 3-4 hours. In another embodiment, the electromagnetic energy may be applied at a power of 100-1000W, 1KW-10KW, or 5KW-1MW. In another embodiment, the radiofrequency may comprise a frequency between about 1-300 MHz, 300 kHz-3 MHz, 3-30 MHz, 30-300 MHz, 13, 13.56, 27, 27.12, 40, or 40.68 MHz. In another embodiment, the radiofrequency may penetrate the biomass to about 0.001 to 2.0 meters thickness. In another embodiment, the biomass may be heated to a temperature of at least about 1-300° C., 50° C.-100° C., 60° C.-130° C., 80° C.-175° C., or 100° C.-240° C. . In another embodiment, the biomass may be treated with radiofrequency for at least about 1 minute to 100 hours, 1-60 minutes, 1-24 hours, 5-10 minutes, 5-30 minutes, 10-50 minutes, 5 minutes to 3 hours, 1-3 hours, 2-4 hours, 3-6 hours, or 4-8 hours.

In one embodiment, the method may further comprise washing the treated biomass. In another embodiment, the washing may comprise washing the biomass with a liquid non-solvent for cellulose that is miscible with water and the ionic liquid (IL). In another embodiment, the liquid non-solvent used for washing may be water, an alcohol, acetonitrile or a solvent which dissolves the IL and thereby may extract the IL from the biomass. In another embodiment, the alcohol may be ethanol, methanol, butanol, propanol, or mixtures thereof.

In one embodiment, the ionic liquid may be recovered from the liquid non-solvent by a method selected from one or more of activated charcoal treatment, distillation, membrane separation, electro-chemical separation techniques, sold-phase extraction liquid-liquid extraction, or a combination thereof. In another embodiment, the ionic liquid may be recovered from the liquid non-solvent by application of electromagnetic heating, optionally radiofrequency heating, that dehydrates the ionic liquid. In another embodiment, the method may comprise the further step of reusing the recovered IL for treating more biomass, optionally wherein at least 90, 91, 92, 93, 94, 95, 96, 97, 98, or 99% of the IL may be recovered. In another embodiment, the ionic liquid may have a water content not exceeding about 1, 2, 3, 4, 5, 6, 7, 8, 9, 10, 11, 12, 13, 14, 15, 16, 17, 18, 19, 20, 21, 22, 23, 24, or 25%.

In one embodiment, the method comprises incubating the biomass in a sufficient amount of an ionic liquid (IL) for a sufficient time to swell the biomass.

In one embodiment, the biomass may be subjected to additional heating with agitation, ultrasonics heating, electromagnetic (EM) heating, convective heating, conductive heating, microwave irradiation, or a combination thereof, optionally with intermittent agitation during heating.

In one embodiment, the ionic liquid may be molten at a temperature ranging from about 10° C. to 160° C. and comprises cations or anions. In another embodiment, the ionic liquid may comprise a cation structure that includes ammonium, sulfonium, phosphonium, lithium, imidazolium, pyridinium, picolinium, pyrrolidinium, thiazolium, triazolium, oxazolium, or combinations thereof. In another embodiment, the ionic liquid may comprise a cation selected from imidazolium, pyrrolidinium, pyridinium, phosphonium, ammonium, or a combination thereof. In another embodiment, the ionic liquid (IL) may be 1-n-butyl-3-methylimidazolium chloride, 1-allyl-3-methyl imidazolium chloride, 3-methyl-N-butylpyridinium chloride, 1-ethyl-3-methyl imidazolium acetate, 1-ethyl-3-methyl imidazolium propionatem, or combinations thereof.

In one embodiment, the method may be a continuous process. In another embodiment, the method may be a batch process.

In one embodiment, the conditions of said biomass undergoing radiofrequency (RF) heating may be monitored by means of sensors, optionally a liquid flow rate sensor, thermocouple sensor, temperature sensor, salinity sensor, or combinations thereof. In another embodiment, the method may comprise adjusting the amount of ionic liquid, the time of incubation, or the temperature of the biomass.

In one embodiment, the biomass may be not dissolved in the ionic liquid.

In one embodiment, the biomass may be dissolved in the ionic liquid. In another embodiment, the dissolved biomass, optionally cellulose or hemicellulose, may be regenerated by the use of anti-solvents. In another embodiment, the anti-solvent may be water, methanol, ethanol, acetate, or mixtures thereof.

In one embodiment, the method may further comprise treating said treated biomass with biochemical reagents, optionally an enzyme, to convert the cellulose and hemicellulose to sugars, optionally hexose and pentose sugars. In another embodiment, the biochemical reagent used to convert the cellulose and hemicellulose may be an enzyme, optionally an enzyme mixture of hemicellulases, cellulases, endo-glucanases, exo-glucanases, and 1-β-glucosidases. In another embodiment, the cellulase may be cellobiohydrolase, endocellulase, exocellulase, cellobiase, endo-beta-1,4-glucanase, beta-1,4-glucanase, or mixtures thereof.

In another embodiment, the hemicellulase may be laminarinase, lichenase, xylanase, or mixtures thereof. In another embodiment, the enzyme mixture may further comprise xylanases, arabinases, or mixtures thereof. In another embodiment, the biochemical reagents are thermophilic enzymes, optionally enzymes that are active up to about 70° C. In another embodiment, the biomass may be heated to at least about 50-100° C., 40° C., 55° C., or 70° C.

In another embodiment, the sugars may be converted to renewable fuels, chemicals and materials, optionally ethanol, butanol, lactic acid, gasoline, biodiesel, methane, hydrogen, electricity, plastics, composites, protein, drugs, fertilizers or other components thereof. In another embodiment, the chemicals may be succinic acid, glycerol, 3-hydropropoionic acid, 2,5-dimethylfuran (DMF), 5-hydroxymethyl furfural (HMF), furfural, 2,5-furandicarboxylic acid, itaconic acid, levulinic acid, aldehydes, alcohols, amines, terephthalic acid, hexamethylenediamine, isoprene, polyhydroxyalkanoates, 1,3-propanediol, or mixtures thereof.

In one embodiment, the method may further comprise recovering the enzymes.

In one embodiment, the treatment produces a solid residue may comprise proteins and lignin. In another embodiment, the lignin may be converted to fuels, chemicals, polymers, or mixtures thereof.

In one embodiment, the method further comprises treating said treated biomass with chemical reagents to convert the cellulose and hemicellulose to sugars, optionally hexose and pentose sugars. In another embodiment, the sugars may be converted to chemicals, optionally succinic acid, glycerol, 3-hydropropoionic acid, 2,5-dimethylfuran (DMF), 5-hydroxymethyl furfural (HMF), furfural, 2,5-furandicarboxylic acid, itaconic acid, levulinic acid, aldehydes, alcohols, amines, terephthalic acid, hexamethylenediamine, isoprene, polyhydroxyalkanoates, 1,3-propanediol, or mixtures thereof.

In another embodiment, a method for disruption of the structure of a lignocellulosic biomass may comprise incubating a biomass in an ionic liquid (IL) and applying radiofrequency (RF) heating and ultrasonics, electromagnetic (EM), convective, conductive heating, or combinations thereof.

In another embodiment, a method for conversion of the carbohydrates of biomass to sugars may comprise: (a) mixing biomass in an ionic liquid (IL) to form a biomass/IL slurry; (b) applying radio frequency (RF) heating to the biomass/IL slurry to heat to a target temperature range, optionally 50-220° C.; (c) applying ultrasonics, electromagnetic (EM), convective, conductive heating, or combinations thereof to the biomass/IL slurry to maintain the slurry at said target temperature range; (d) washing the treated biomass; (e) hydrolyzing the treated biomass to yield sugars, optionally pentose and hexose sugars, and release lignin.

In another embodiment, a method for the conversion of cellulose to sugar may comprise: (a) mixing biomass in an ionic liquid (IL) to form a biomass/IL slurry; (b) applying radio frequency (RF) heating to the biomass/IL slurry to heat to a target temperature range, optionally 50-220° C.; (c) applying ultrasonics, electromagnetic (EM), convective, conductive heating, or combinations thereof to the biomass/IL slurry to maintain the slurry at said target temperature range; (d) precipitating amorphous cellulose and/or cellulose of reduced crystallinity by admixture with an anti-solvent; and (e) adding cellulase to the cellulose precipitate under conditions which promote the hydrolysis of cellulose to sugars. In another embodiment, the heating may be electromagnetic heating, heating by use of a variable frequency in the electromagnetic spectrum, variable frequency heating, or a combination thereof.

In another embodiment, a method for treatment of biomass may comprise: (a) incubating a biomass in a sufficient amount of an ionic liquid (IL) for a sufficient time and temperature to swell the biomass without dissolution of the biomass in the IL; (b) applying radio frequency (RF) heating to the biomass/IL slurry to heat to a target temperature range, optionally 50-220° C.; (c) applying ultrasonic heating to the biomass/IL slurry to maintain the slurry at said target temperature range; (d) washing the treated biomass with a liquid non-solvent for cellulose that may be miscible with water and the IL; and (e) contacting said washed treated biomass with an aqueous buffer comprising enzymes capable of hydrolyzing cellulose and hemicellulose to produce sugars, optionally hexose and pentose sugars. In another embodiment, the heating may be electromagnetic heating, heating by use of a variable frequency in the electromagnetic spectrum, variable frequency heating, or a combination thereof.

In another embodiment, a method for conversion of the carbohydrates of biomass to sugars may comprise: (a) mixing biomass in an ionic liquid (IL) to swell the biomass; (b) applying radio frequency (RF) heating to the biomass to heat to a target temperature range, optionally 50-220° C.; (c) applying ultrasonics, electromagnetic (EM), convective, conductive heating, or combinations thereof to the biomass to maintain the biomass at said target temperature range; (d) washing the treated biomass; (e) hydrolyzing the treated biomass to yield sugars, optionally pentose and hexose sugars, and release lignin.

In another embodiment, a method for the conversion of cellulose to sugar may comprise: (a) mixing biomass in an ionic liquid (IL) to swell the biomass; (b) applying radio frequency (RF) heating to the biomass to heat to a target temperature range, optionally 50-220° C.; (c) applying ultrasonics, electromagnetic (EM), convective, conductive heating, or combinations thereof to the IL swelled biomass to maintain the biomass at said target temperature range; (d) precipitating amorphous cellulose and/or cellulose of reduced crystallinity by admixture with an anti-solvent; and (e) adding cellulase to the cellulose precipitate under conditions which promote the hydrolysis of cellulose to sugars. In another embodiment, the heating may be electromagnetic heating, heating by use of a variable frequency in the electromagnetic spectrum, variable frequency heating, or a combination thereof.

In another embodiment, a method for treatment of biomass may comprise: (a) incubating a biomass in a sufficient amount of an ionic liquid (IL) for a sufficient time and temperature to swell the biomass without dissolution of the biomass in the IL; (b) applying radio frequency (RF) heating to the biomass to heat to a target temperature range, optionally 50-220° C.; (c) applying ultrasonic heating to the biomass to maintain the biomass at said target temperature range; (d) washing the treated biomass with a liquid non-solvent for cellulose that may be miscible with water and the IL; and (e) contacting said washed treated biomass with an aqueous buffer comprising enzymes capable of hydrolyzing cellulose and hemicellulose to produce sugars, optionally hexose and pentose sugars. In another embodiment, the heating may be electromagnetic heating, heating by use of a variable frequency in the electromagnetic spectrum, variable frequency heating, or a combination thereof.

In one embodiment, the liquid non-solvent used for washing may be water, an alcohol, acetonitrile or a solvent which dissolves the IL and thereby extracts the IL from the biomass. In another embodiment, the alcohol may be ethanol, methanol, butanol, propanol, or mixtures thereof. In another embodiment, the method may further comprise recovering the IL from the liquid non-solvent by a method selected from activated charcoal treatment, distillation, membrane separation, electro-chemical separation techniques, sold-phase extraction liquid-liquid extraction, or a combination thereof. In another embodiment, the heating may be electromagnetic heating, heating by use of a variable frequency in the electromagnetic spectrum, variable frequency heating, or a combination thereof.

In one embodiment, the treatment may produce a solid residue comprising proteins and lignin. In another embodiment, the lignin may be converted to fuels, chemicals, polymers, or mixtures thereof. In another embodiment, the wash may be recovered and treated with RF heating to dehydrate the ionic liquid.

In another embodiment, a method of acidolysis of biomass may comprise: (a) mixing biomass in an ionic liquid (IL) to form a biomass/IL slurry; (b) adding an acid, optionally sulfuric acid, hydrochloric acid, nitric acid, or phosphoric acid, optionally lowering the pH of the slurry below pH 7, optionally a pH between 1-6; (c) applying radio frequency (RF) heating to the biomass/IL slurry to heat to a target temperature range, optionally 50-220° C.; and (d) applying ultrasonic heating to the biomass/IL slurry to maintain the slurry at said target temperature range.

The invention also provides a method of acidolysis of biomass comprising: (a) mixing biomass in an ionic liquid (IL) to form a biomass/IL slurry; (b) adding an acid, optionally sulfuric acid, hydrochloric acid, nitric acid, or phosphoric acid, optionally lowering the pH of the slurry below pH 7, optionally a pH between 1-6; (c) applying radio frequency (RF) heating to the biomass/IL slurry to heat to a target temperature range, optionally 50-220° C.; (d) applying ultrasonic heating to the biomass/IL slurry to maintain the slurry at said target temperature range; (e) optionally washing the treated biomass; and (f) recovering sugars, optionally pentose and hexose sugars, and released lignin. In another embodiment, the method may further comprise addition of a base, optionally NaOH or KOH to neutralize the pH of the biomass/IL slurry.

In another embodiment, a method of acidolysis of biomass may comprise: (a) mixing biomass in an ionic liquid (IL) to swell the biomass; (b) adding an acid, optionally sulfuric acid, hydrochloric acid, nitric acid, or phosphoric acid, optionally lowering the pH of the biomass below pH 7, optionally a pH between 1-6; (c) applying radio frequency (RF) heating to the biomass to heat to a target temperature range, optionally 50-220° C.; and (d) applying ultrasonic heating to the biomass to maintain the biomass at said target temperature range.

The invention also provides a method of acidolysis of biomass comprising: (a) mixing biomass in an ionic liquid (IL) to swell the biomass; (b) adding an acid, optionally sulfuric acid, hydrochloric acid, nitric acid, or phosphoric acid, optionally lowering the pH of the biomass below pH 7, optionally a pH between 1-6; (c) applying radio frequency (RF) heating to the biomass to heat to a target temperature range, optionally 50-220° C.; (d) applying ultrasonic heating to the IL swelled biomass to maintain the biomass at said target temperature range; (e) optionally washing the treated biomass; and (f) recovering sugars, optionally pentose and hexose sugars, and released lignin. In another embodiment, the method may further comprise addition of a base, optionally NaOH or KOH to neutralize the pH of the biomass.

In another embodiment, the heating may be electromagnetic heating, heating by use of a variable frequency in the electromagnetic spectrum, variable frequency heating, or a combination thereof. In a further embodiment, the pH may be about 1, 2, 3, 3.5, 4, 4.5, 5, 5.5, 5.8, 6, 6.5, or 6.8. In yet another embodiment, the pH may be about 1-3, 2-4, 3-5, 2-6, 3.5-4.5, or 4-6. In a further embodiment, the temperature may be about 120° C., 130° C., 140° C., 150° C., 120° C.-150° C., 130° C.-140° C., or 100° C.-150° C.

In one embodiment, a system for treating biomass may comprise at least one electromagnetic (EM) oven; and a moving platform comprising at least one conveyor belt, the moving platform configured to receive biomass on a conveyor belt at a first end of the moving platform, to move the biomass through an electromagnetic (EM) oven thereby treating the biomass by radio frequency treatment in combination with ionic liquids, and, optionally, comprising a sensor network coupled to a feedback system.

In one embodiment, a system for treating biomass may comprise a mixing zone, wherein the biomass may be admixed with an ionic liquid, coupled to a variable RF processing zone comprising a variable upper electrode and a fixed lower electrode, wherein the biomass may be subjected to variable RF treatment, coupled to a washing zone, wherein the biomass may be washed, and, optionally, comprising a sensor network coupled to a feedback system.

In one embodiment, a system for treating biomass may comprise a mixing zone, wherein the biomass is admixed with an ionic liquid, coupled to an electromagnetic (EM), optionally radiofrequency, processing zone comprising a variable upper electrode and a fixed lower electrode, wherein the biomass is subjected to electromagnetic (EM), optionally radiofrequency, treatment, coupled to a washing zone, wherein the biomass is washed, and, optionally, comprising a sensor network coupled to a feedback system.

In one embodiment, a system for treating biomass may comprise a reactor vessel coupled to a sensor network coupled to a feedback means for controlling the time, temperature, pressure, and water content of the interior of the reactor vessel.

In yet another embodiment, a method and apparatus for processing biomass (e.g., woody biomass, feedstock, agricultural biomass) using ionic liquid together with electromagnetic waves in the radiofrequency and lower microwave frequency range for effective uniform processing of biomass (e.g., woody biomass, feedstock, and agricultural biomass) at high solids loadings (e.g., >30% w/w). Given that wood, cellulose and lignin are poor conductors of heat, operating a reactor with high solids loading based on heating through conduction or convection requires reactors with large volumes/surface areas. In these situations, radiofrequency (RF) waves can be used to heat the ionic liquids or other fluids with ionic contents or polar fluids, even when the fluids are dispersed in biomass or its components. Coupled with a precise control system, the residence time and temperature of the mixture in the reactor can be controlled and the process successfully implemented at different scales. The systems may be coupled to a membrane filter. The membrane filter may be a membrane process comprising ultra-filtration, nano-filtration, reverse osmosis, prevaporation, or a combination thereof. The systems may also allow for the separation of gas from the fluid, such as fuel gas.

In one embodiment, the invention provides a method for processing lignocellulosic biomass, one more of its constituents, algae, coal, cellulose, lignin, for conversion to fuels, chemicals, materials and other value added products. In another embodiment, the invention provides methods for treating biomass slurries, solutions, and suspensions utilizing radiofrequency electromagnetic irradiation and/or ultrasonic heating for effective and amenable conversion of biomass and derived products to renewable fuels, chemicals, and materials. In another embodiment, the invention provides systems for treating biomass slurries, solutions, and suspensions utilizing electromagnetic irradiation and/or ultrasonic heating for effective and amenable conversion of biomass and derived products to renewable fuels, chemicals, and materials.

In certain embodiments, this invention relates to the development of radiofrequency dielectric treatment of biomass. In some embodiments, this invention relates to the utilization of dielectric heating treatment for ionic liquid treatment process. In some embodiments, this relation related to the invention of effective low to high solids loading treatment of biomass using ionic liquids, aqueous solutions, acidic-basic solutions, chemical-biological catalysts using dielectric heating method and apparatus for production of renewable fuels, chemicals and materials. In some embodiments, this invention relates to the concentration of non-volatile ionic liquids solutions through the utilization of RF wave heating of dilute aqueous or non-aqueous solutions consisting of ionic liquids. In some embodiments this invention relates to the development of method and apparatus for batch or continuous treatment of biomass treatment, treatment, washing, and recovery processes.

In one embodiment, a method for treating biomass may comprise mixing biomass with an ionic liquid (IL) to form a slurry, heating said biomass/IL slurry with electromagnetic energy (e.g., radiofrequency energy) and ultrasonic heating to yield treated biomass, washing the treated biomass, and contacting said treated biomass with an enzyme to convert the treated biomass to polysaccharides and release bound proteins and lignin. In one embodiment, the method may comprise uniform heat penetration by the radio frequency heating. In another embodiment, the ionic liquid may be capable of disrupting hydrogen-bonding in the structure of cellulose or hemicellulose. In one embodiment, the ionic liquid is molten during incubation. In another embodiment, the ionic liquid (IL) may be recovered and reused. In a further embodiment, the IL may be dehydrated by the application of radiofrequency heating. In another embodiment, the enzymes used in hydrolysis may be recovered and reused.

In one embodiment, a method for treating biomass may comprise mixing biomass with an ionic liquid (IL) to swell the biomass, heating said biomass with electromagnetic energy (e.g., radiofrequency energy) and ultrasonic heating to yield treated biomass, washing the treated biomass, and contacting said treated biomass with an enzyme to convert the treated biomass to polysaccharides and release bound proteins and lignin. In one embodiment, the method may comprise uniform heat penetration by the radio frequency heating. In another embodiment, the ionic liquid may be capable of disrupting hydrogen-bonding in the structure of cellulose or hemicellulose. In one embodiment, the ionic liquid is molten during incubation. In another embodiment, the ionic liquid (IL) may be recovered and reused. In a further embodiment, the IL may be dehydrated by the application of radiofrequency heating. In another embodiment, the enzymes used in hydrolysis may be recovered and reused.

In another embodiment, the time and temperature during the step of IL-incubation of the biomass may be optimized to sufficiently swell matrices of the biomass to enhance the penetration of hydrolyzing enzymes and water during a hydrolysis step. In a further embodiment, the incubating step comprises incubating the biomass in an ionic liquid for a time ranging from about 5 minutes to 8 hours, optionally about 5-30 minutes, heating with a combination of radiofrequency and ultrasonics, EM, convective, conductive heating, or combinations thereof at a temperature ranging from about 50° C.-200° C., optionally for about 5-30 minutes. In a further embodiment, the treated biomass may be washed and then undergo hydrolysis to yield pentose and hexose sugars and lignin. In another embodiment, the sugars may be converted to renewable fuels, chemicals, optionally ethanol, butanol, lactic acid, gasoline, biodiesel, methane, hydrogen, plastics, proteins, drugs, or fertilizers.

In one embodiment, the biomass may be dissolved in an ionic liquid (IL). In another embodiment, the dissolved cellulose may be regenerated by the use of anti-solvents. In a further embodiment, the antisolvent may be water, ethanol, methanol, acetone, or mixtures thereof.

In one embodiment, the biomass may be mixed with an ionic liquid (IL) to form a biomass/IL slurry, suspension, or suspension (in liquid phase). In a further embodiment, the biomass may be mixed with an ionic liquid (IL) to swell but not dissolve the biomass.

In one embodiment, the reactor may be loaded with a high level of biomass. In another embodiment, the biomass-ionic liquid slurry comprises high solids loadings at least about 10%, 20%, 30%, 40%, 50%, 60%, 70%, 80%, 90%, or 95% w/w. In one embodiment, the reactor may be loaded with a high level of biomass. In another embodiment, the biomass may comprises high solids loadings at least about 10%, 20%, 30%, 40%, 50%, 60%, 70%, 80%, 90%, or 95% w/w. In a further embodiment, the biomass may be loaded at high solids loading at approximately 30% w/w.

In one embodiment, the biomass may be comminuted to smaller sized particles. In another embodiment, the biomass may be comminuted to smaller sized particles prior to mixing with an ionic liquid. In a further embodiment, the biomass may be comminuted to small particles about 0.1-20 mm, 0.1-2 mm, or about 5 mm in size.

In another embodiment, a system and method for treatment of biomass may employ a variable frequency in the electromagnetic spectrum in combination with an ionic liquid. A system and method for treatment of biomass may employ a variable frequency in the electromagnetic spectrum in combination with an ionic liquid and an acid. The treated biomass may be further processed to yield renewable fuels, chemicals and materials, optionally ethanol, butanol, lactic acid, gasoline, biodiesel, methane, hydrogen, electricity, plastics, composites, protein, drugs, fertilizers or other components thereof.

BRIEF DESCRIPTION OF THE DRAWINGS

FIG. 2A is a schematic diagram of an electromagnetic (EM) oven interior showing electrode positions.

FIG. 2B is a schematic diagram of a dielectric radiofrequency system.

FIG. 2C is a schematic side profile of sensor for temperature process state measurement during electromagnetic (EM) wave processing of biomass.

FIG. 3 depicts an electronic configuration of a water molecule and (b) dipole reorientation in an electric field.

FIG. 4 depicts exemplary cation and anion components of ionic liquids.

FIG. 5A is a schematic diagram of a continuous belt press radiofrequency apparatus of biomass processing.

FIG. 5B is a schematic diagram of a lignocellulosic biomass processing in a radiofrequency treating system comprising an Archimedes screw in a conduit with three zones.

DETAILED DESCRIPTION OF THE PREFERRED EMBODIMENTS

Figure 1A:
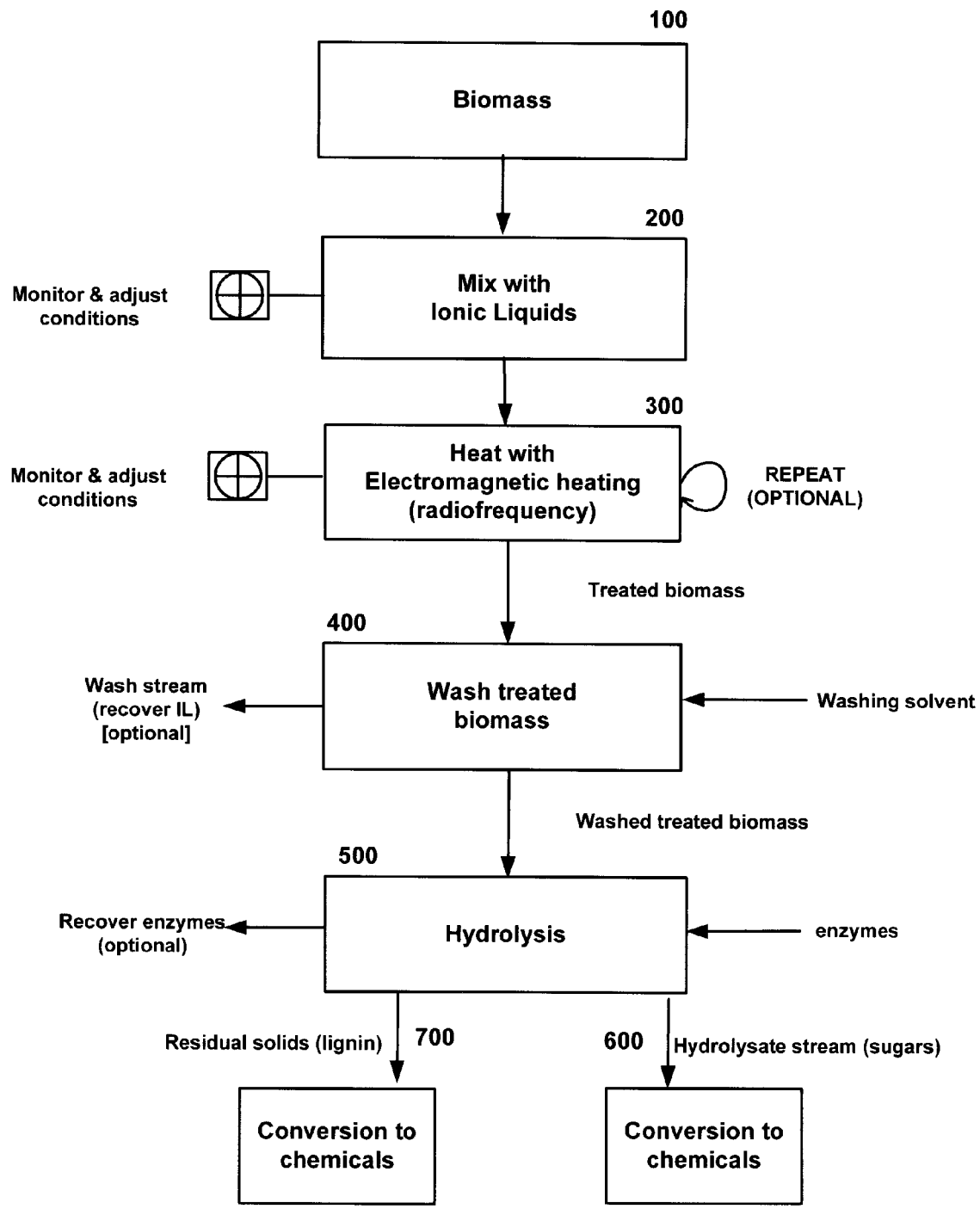
FIG. 1A depicts an exemplary method for processing biomass comprising mixing with ionic liquid, heating by radio frequency, optionally repeated, washing the biomass, optionally recovering the IL, hydrolysis (e.g., addition of cellulase and hemicellulases) of the cellulose and hemicellulose to their constituent monomeric sugars (e.g., five and six carbon sugars), optionally recovery of the added enzymes, separation of the hydrolystate stream comprising sugars for further processing to produce chemicals or biofuels and the residual solids comprising proteins and lignin for further processing to produce chemicals or biofuels. The ionic liquid and enzymes may be reclaimed and reused.

In order that the invention herein described may be fully understood, the following detailed description is set forth.

Various embodiments of the invention are described in detail and may be further illustrated by the provided examples. Additional viable variations of the embodiments can easily be envisioned.

Definitions

Unless defined otherwise, all technical and scientific terms used herein have the same meaning as those commonly understood by one of ordinary skill in the art to which this invention belongs.

As used in the description herein and throughout the claims that follow, the meaning of "a," "an," and "the" includes plural reference unless the context clearly dictates otherwise.

"Biomass," as used herein, refers broadly to any biological material. Biomass encompasses substrates containing organic components which can be used in production of renewable fuels, chemicals and materials such as ethanol, butanol, lactic acid, gasoline, biodiesel, methane, hydrogen, plastics, composites, protein, drugs, fertilizers or other components thereof. Biomass may be agricultural residues, optionally corn stover, wheat straw, bagasse, rice hulls, or rice straw; wood and forest residues, optionally pine, poplar, douglas fir, oak, saw dust, paper/pulp waste, or wood fiber; feedstock (e.g., woody biomass and agricultural biomass); kudzu; algae; coal; cellulose, lignin, herbaceous energy crops, optionally switchgrass, reed canary grass, or miscanthus; lingocellulosic biomass, optionally comprising lignin, cellulose, and hemicellulose; plant biomass; or mixtures thereof. Biomass may be lignocellulosic biomass comprising cellulose, hemicellulose, and lignin.

"Ionic liquids" as used herein, refers broadly to room temperature liquids that contain only ions and are molten salts stable up to 300° C. Sheldon (2001) *Chem. Commun.* 23: 2399-2407.

"Lignocellulosic biomass" as used herein, refers broadly to plant biomass that is composed of cellulose, hemicellulose, and lignin. The carbohydrate polymers (e.g., cellulose and hemicelluloses) are tightly bound to the lignin. Lignocellulosic biomass can be grouped into four main categories: agricultural residues (e.g., corn stover and sugarcane bagasse), dedicated energy crops, wood residues (e.g., sawmill and paper mill discards), and municipal paper waste.

"Pretreatment of biomass," as used herein, refers broadly to a process of changing the physiochemical structure of biomass to make it amenable for efficient conversion to their monomeric valuable products.

"Radiofrequency (RF) heating," as used herein, refers broadly to application of electromagnetic field to biomass/products/dielectric materials at frequencies from about 1-300 MHz.

"Electromagnetic energy (EM)," as used herein, refers broadly to a form of energy that is reflected or emitted from objects in the form of electrical and magnetic waves that can travel through space. There are many forms of electromagnetic energy including gamma rays, x rays, ultraviolet radiation, visible light, infrared radiation, microwaves, and radio waves (radiofrequency).

"Ultrasonics" or "ultrasonic waves," as used herein, refers broadly to sound waves (mechanical waves) with high frequency about between 15 kHz to 40 kHz (e.g., about 20 kHz) and low amplitude about between 0.0001-0.025 mm.

Treatment of Biomass Using Combination of Ionic Liquids and RF Heating

The present invention relates to the processing of biomass, lignocellulosic biomass, one more of its constituents, algae, or coal, for conversion to fuels, chemicals, materials and other value added products. The invention incorporates systems and processes useful for treating biomass slurries, solutions, and suspensions utilizing radiofrequency electromagnetic irradiation for effective and amenable conversion of biomass and derived products to renewable fuels, chemicals, and materials. The present invention provides for an uniform heat penetrable radio frequency processing of biomass and related products. The present invention provides a system including an apparatus used for biomass processing using radio frequency treating in combination with ionic liquids as well as methods and processes for optimization.

The invention provides a method for conversion of the carbohydrates of lignocellulose to sugars with improvements in yield and rate of sugar production using ionic liquid (IL) treatment in combination with RF heating. This treatment strategy substantially improves the efficiency (in terms of yield and reaction rates) of hydrolysis (e.g., saccharification) of lignocellulosic biomass. Other features of this IL-treatment method that have a major impact on the overall economics of sugar production from biomass, in stark contrast to prior art methods, are its (i) ability to process a variety of lignocellulosic biomass sources with ILs capable of disrupting native cellulose structure (ii) ability to handle large biomass to IL ratios during incubation (iii) ability to accomplish saccharification at very low enzyme loadings (iv) ability to perform well with large biomass particles (v) potential for total recovery (through facile means) and multiple reuse of the IL employed to treat the biomass, (vi) ability to produce a hydrolysate free of compounds that can inhibit the downstream processing of the constituent sugars, (e.g., ethanol and lactic acid production), and (vii) allows for recovering most of the lignin in biomass following saccharification.

The biomass may be comminuted to smaller sized particles prior to mixing with an ionic liquid and treatment. For example, the biomass may be ground, chopped, or otherwise comminuted to small particles about 0.1-2 mm.

FIG. 1A is a schematic of a method for producing sugars from biomass. Biomass includes but is not limited to wheat straw, waste rice straw, algae, kudzu, agricultural waste, municipal waste, corn stover, wood waste, agricultural residues, optionally corn stover, wheat straw, bagasse, rice hulls, or rice straw; wood and forest residues, optionally pine, poplar, douglas fir, oak, saw dust, paper/pulp waste, or wood fiber; algae; herbaceous energy crops, optionally switchgrass, reed canary grass, or miscanthus, biomass that is lingocellulosic biomass, optionally comprising lignin, cellulose, and hemicellulose; and biomass that is a plant biomass. The biomass may be added to a high solids loading (e.g., >30% w/w). The biomass is mixed with ionic liquid (IL) to swell but not dissolve the biomass and heated using radio frequency (RF) energy. Both the mixing with ionic liquid and heating with RF may be monitored for sufficient penetration and uniform heating and the conditions (e.g., time, pressure, heat, intensity of RF energy) may be adjusted as necessary to maintain sufficient penetration and uniform heating of the biomass. Optionally, after the application of RF heating, ultrasonics, electromagnetic heating (EM) (e.g., radiofrequency), convective, conductive heating, or combinations thereof may be used to maintain the temperature of the IL swelled biomass. Following treatment (e.g., incubation with ionic liquid and heating), the treated biomass may be washed and then undergo cellulose hydrolysis (cellulolysis) to break down the cellulose and hemicellulose into sugars and free the lignin. In the hydrolysis process, the cellulose and hemicellulose may undergo a chemical treatment (e.g., using acids) or a biochemical treatment (e.g., enzymatic digestion). The sugars may then be separated from residual materials (e.g., lignin). The sugar solution may then be converted to chemicals (e.g., ethanol, lactic acid, succinic acid). Treatment with has a major influence on the reducing the cost in both prior (e.g., size reduction) and subsequent (e.g. enzymatic hydrolysis) operations in sugar production and improving yields.

Figure 1B:
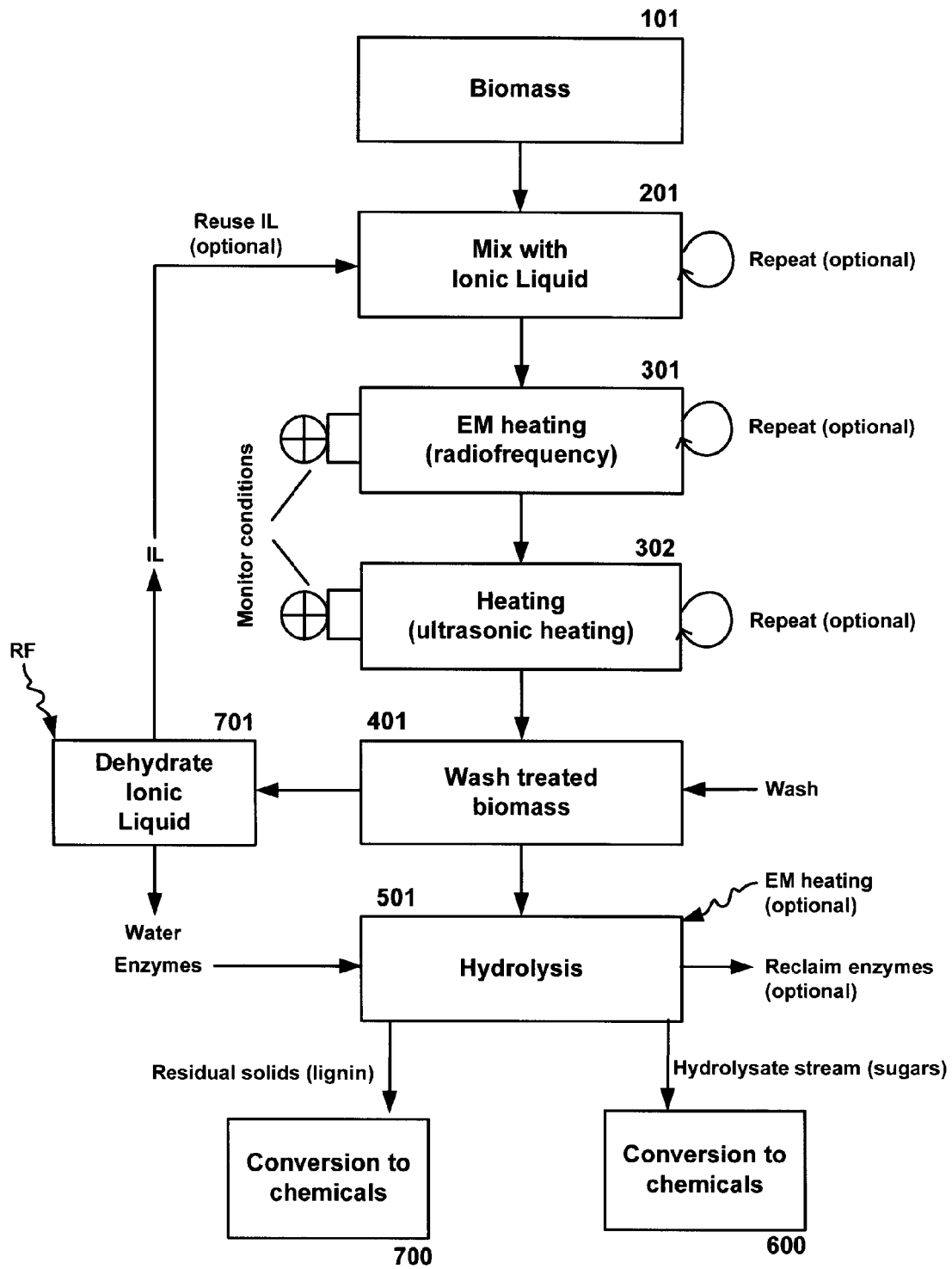
FIG. 1B depicts an exemplary method for processing biomass comprising mixing with ionic liquid, heating by radio frequency irradiation to reach a target temperature range, optionally repeated, maintaining the temperature of the IL swelled biomass using of ultrasonics (e.g., sound waves with high frequency about between 15 kHz to 40 kHz, or 20 kHz and low amplitude about between 0.0001-0.025 mm), electromagnetic irradiation (EM) (e.g., radiofrequency), convective, conductive heating, or combinations thereof, optionally about 5-30 minutes, optionally repeated, washing the biomass, optionally recovering the IL and dehydrating the IL by application of radiofrequency heating, hydrolysis (e.g., addition of celluase and hemicellulases) of the cellulose and hemicellulose to their constituent monomeric sugars (e.g., five and six carbon sugars), optionally recovery of the added enzymes, separation of the hydrolystate stream comprising sugars for further processing to produce chemicals or biofuels and the residual solids comprising proteins and lignin for further processing to produce chemicals or biofuels. The enzymes may be reclaimed and reused.

FIG. 1B is a schematic of a method for producing sugars from biomass. The biomass is mixed with ionic liquid (IL) to form a IL swelled biomass and heated using electromagnetic energy, comprising two phases. In the first Initial Phase, radio frequency (RF) energy is used to heat the biomass to a target temperature (or temperature range). In the second, Maintenance Phase, of ultrasonics (sound waves with high frequency about between 15 kHz to 40 kHz (e.g., about 20 kHz) and low amplitude about between 0.0001-0.025 mm), electromagnetic irradiation (EM) (e.g., radiofrequency), convective, conductive heating, or combinations thereof may be used to maintain the heat at a target temperature (e.g., 50-70° C.). Both the mixing with ionic liquid and heating steps may be monitored for sufficient penetration and uniform heating and the conditions (e.g., time, pressure, heat, intensity of RF energy) may be adjusted as necessary to maintain sufficient penetration and uniform heating of the biomass. Following treatment (e.g., incubation with ionic liquid and electromagnetic irradiation (EM) (e.g., radiofrequency) heating), the treated biomass may be washed. The wash effluent may be collected and the ionic liquid dehydrated by the application of RF energy. The RF energy heats IL faster than it heats water because of a stronger dipole moment in IL. Without being bound to a specific theory, the inventors surprisingly discovered that the ions try to align with the electromagnetic irradiation (EM) (e.g., radiofrequency) waves, always changing creating a dipole moment. See FIG. 3. The IL heated by RF acts as a substrate for the water to heat and evaporate from the IL wash effluent. The washed treated biomass may then undergoes cellulose hydrolysis (cellulolysis) to break down the cellulose and hemicellulose into sugars and free the lignin. In the hydrolysis process, the cellulose and hemicellulose may undergo a chemical treatment (e.g., using acids) or a biochemical treatment (e.g., enzymatic digestion). The sugars may then be separated from residual materials (e.g., lignin). The sugar solution may then be converted to chemicals (e.g., ethanol, lactic acid, succinic acid). After hydrolysis, the enzymes may be reclaimed. Further, thermophilic enzymes may be used in the hydrolysis step (e.g., enzymes stable and active at about 70° C.). The use of thermophilic enzymes allows for the hydrolysis step to be run at a higher temperature and improves efficiency and yield of the hydrolysis step. For example, mixtures of thermophilic endo- and exo-glycoside hydrolases may be active at high temperatures and acidic pH. The thermophilic enzymes may be isolated from thermophilic bacteria including but not limited to *Sulfolobus solfataricus, Alicyclobacillus acidocaldarius*, and *Thermus thermophilus*. Also, thermophilic cellulases may be used.

Figure 1C:
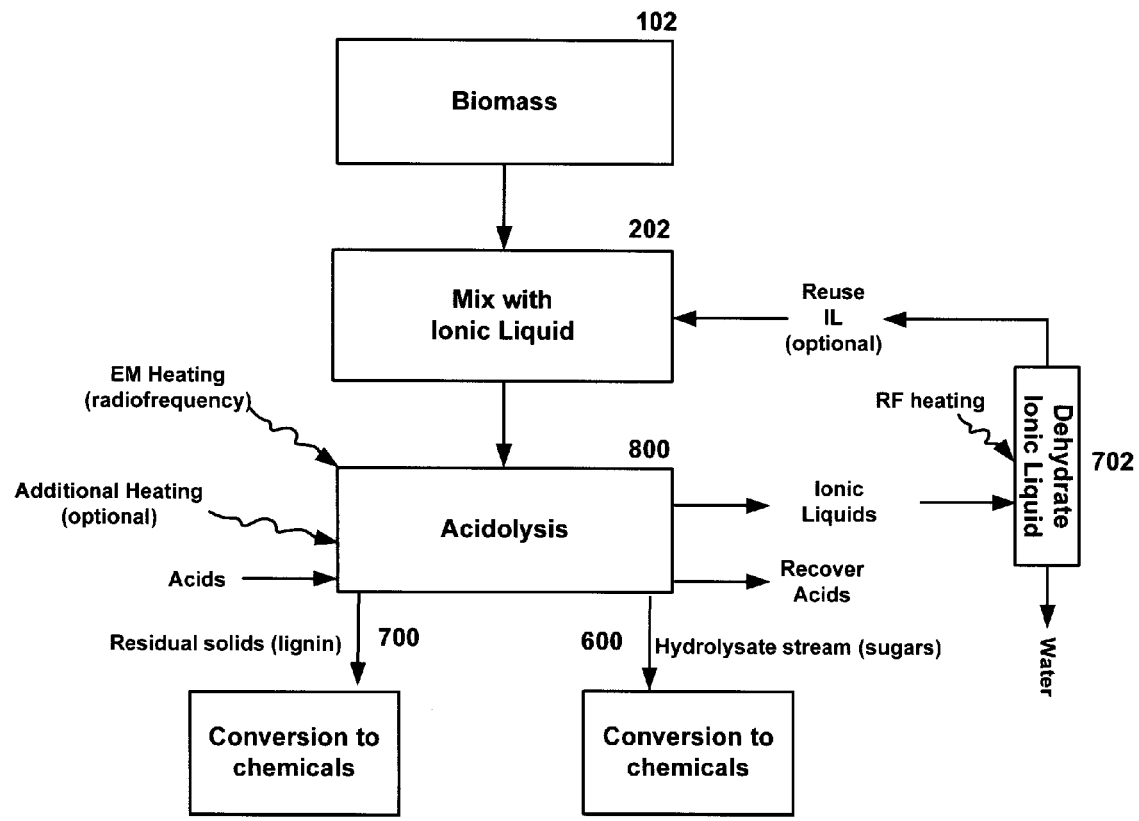
FIG. 1C depicts an exemplary method for processing biomass comprising mixing with ionic liquid and acids, heating by radio frequency irradiation to reach a target temperature range, optionally repeated, maintaining the temperature of the IL swelled biomass using of ultrasonics, electromagnetic irradiation (EM) (e.g., radiofrequency), convective, conductive heating, or combinations thereof, and performing hydrolysis or another reaction. Acid hydrolysis process reduces the cellulose and hemicellulose to their constituent monomeric sugars (e.g., five and six carbon sugars). This is followed by the separation of sugars for further processing to produce chemicals or biofuels and the residual solids comprising proteins and/or lignin for further processing to produce chemicals or biofuels.

FIG. 1C is a schematic of a method for producing sugars from biomass. The biomass is mixed with an ionic liquid (IL) to swell the biomass but not dissolve it and an acid. This mixture of biomass, ionic liquid (IL), and acid may then be heated using electromagnetic energy, comprising two phases. In the first Initial Phase, radio frequency (RF) energy is used to heat the biomass. In the second, Maintenance Phase, of ultrasonics, electromagnetic irradiation (EM) (e.g., radiofrequency), convective, conductive heating, or combinations thereof may be used to maintain the heat at a target temperature (e.g., 120° C., 130° C., 140° C., 150° C., 50-70° C., 50° C.-200° C.). Both the mixing with ionic liquid and heating steps may be monitored for sufficient penetration and uniform heating and the conditions (e.g., time, pressure, heat, intensity of RF energy) may be adjusted as necessary to maintain sufficient penetration and uniform heating of the biomass.

During the acidolysis, the cellulose and hemicellulose is broken down into its constituent sugars (e.g., pentose and hexose sugars). Also, any protein associated with the cellulose and hemicellulose may be liberated creating a proteinaceous residue. Following acidolysis, the wash effluent may be collected and the ionic liquid dehydrated by the application of RF energy. The sugars may then be separated from residual materials (e.g., lignin). The sugar solution may then be converted to chemicals (e.g., ethanol, lactic acid, succinic acid). The lignin may be recovered. Additionally, the acid may be recovered.

Figure 1D:
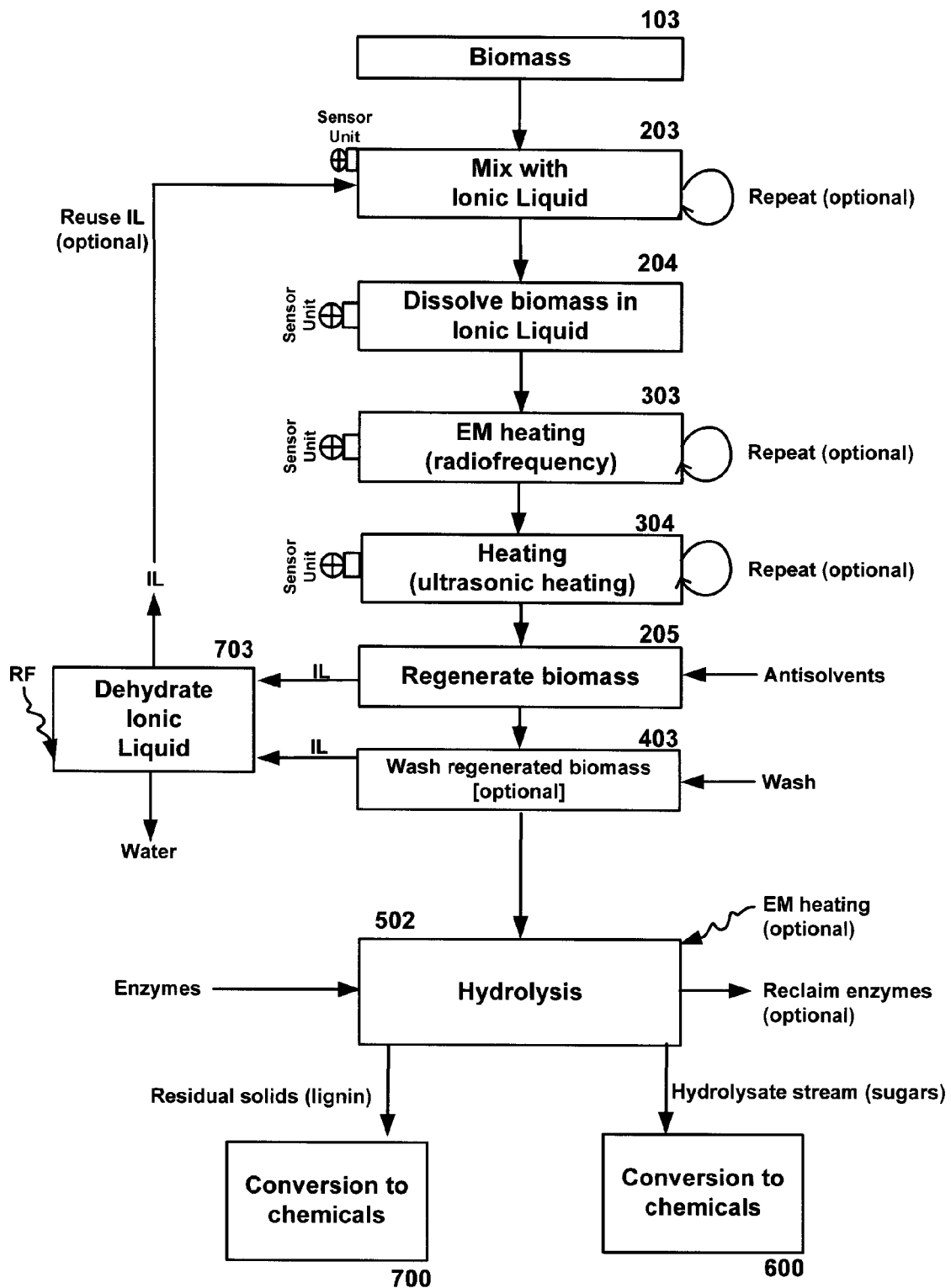
FIG. 1D depicts an exemplary method for processing biomass In another embodiment, a method for processing biomass may comprise mixing with ionic liquid, dissolving the biomass in the ionic liquid, heating by radio frequency, optionally repeated, regenerating the biomass using an antisolvent, optionally water, ethanol, methanol, acetone, or mixtures thereof, optionally recovering the IL, optionally washing the biomass, recovery of the biomass, hydrolysis (e.g., addition of cellulase and hemicellulases) of the cellulose and hemicellulose to their constituent monomeric sugars (e.g., five and six carbon sugars), optionally recovery of the added enzymes, separation of the hydrolystate stream comprising sugars for further processing to produce chemicals or biofuels and the residual solids comprising proteins and lignin for further processing to produce chemicals or biofuels. The ionic liquid and enzymes may be reclaimed and reused.

FIG. 1D is a schematic of a method where biomass may be mixed with an ionic liquid and the biomass may be dissolved in the ionic liquid. Heating of the biomass/IL solution may be carried out by first electromagnetic (EM) (e.g., radiofrequency) heating to reach a target temperature or temperature range (e.g., 50° C.-220° C.) and then heating using ultrasonics, electromagnetic (EM) (e.g., radiofrequency), convective, conductive heating, or combinations thereof at about 50° C. to 200° C. (e.g., 120° C., 130° C., 140° C., 150° C.) for 1-180 minutes, about 5-30 minutes, or 3-4 hours. The conditions may be monitored by use of sensors and adjusted to maintain conditions. The conditions may be monitored and adjusted to maintain uniform heating and sufficient penetration of the biomass by the RF waves. The biomass may be regenerated using an antisolvent, optionally water, ethanol, methanol, acetone, or mixtures thereof. The regenerated biomass may be washed. The IL may be recovered and reused. The regenerated biomass may undergo hydrolysis (e.g., addition of cellulase and hemicellulases) of the cellulose and hemicellulose to their constituent monomeric sugars (e.g., five and six carbon sugars), optionally recovery of the added enzymes. The hydrolystate stream comprising sugars may be separated for further processing to produce chemicals or biofuels and the residual solids comprising proteins and lignin for further processing to produce chemicals or biofuels.

Electromagnetic (EM) Wave Heating

Biomass products at high solids loadings are relatively poor thermal conductors and most conventional thermal treatment processes rely on heat penetration by conduction from the outside to the inside of the product (surface heating). The processing times can be unacceptably long in industrial scale processing operations. Dielectric heating by microwave or radio-frequency (RF) energy shortens thermal processes because heat is generated by direct interaction between electromagnetic energy and the products. RF-heating, in a similar manner to microwave heating, generates heat volumetrically throughout the product. However, RF treating differs from microwave treatment in that the product is placed between two parallel electrodes and an RF field is generated in a directional fashion at right angles to the surface of the electrodes (FIGS. 2*a* and 2*b*). FIG. 2*b* is a schematic diagram of a dielectric radiofrequency system where the IL swelled biomass is placed (or passes) between two electrodes creating a RF heating field. Teflon blocks and Teflon film protect the electrodes and form part of the chamber through which the IL swelled biomass is placed (or passes). FIG. 2*c* is a schematic side profile of a thermocouple/fiber optic jig for temperature measurement during RF wave processing of biomass in one embodiment of the invention.

In addition, the mechanism of dielectric heating with RF field is different from microwave (MW) heating. MW heating occurs mainly via frictional heat generated from the dipolar rotation of free water molecules whereas the predominant mechanism of heating RF is via the depolarization of solvated ions (FIG. 3). MW and RF heating also differ in a number of other respects. As frequency and wavelength are inversely proportional, RF (lower frequency) wavelengths (i.e., 11 m at 27.12 MHz in free space) are much longer than MW (higher frequency) wavelengths (i.e., 0.12 m at 2450 MHz in free space). As electrical waves penetrate into materials attenuation occurs, with the result that the energy of the propagating wave decreases exponentially. Penetration depth (dp) is defined as the depth into the material to which the energy is reduced to 1/e (1/2.72) of the surface energy value. This dp is proportional to wavelength. The free-space wavelength in the RF range (e.g., 13.56, 27.12 and 40.68 MHz) is 20-360 times longer than that of commonly used microwave frequencies (e.g., 915 and 2450 MHz), allowing RF energy to penetrate products more deeply than microwave energy. During RF heating, electromagnetic power can penetrate much deeper into samples without surface over heating or hot/cold spots developing which are more likely to occur with MW heating. Thermal processing with RF heating is, therefore, suitable for processing large products/processes. Wang, et al. (2003) *Journal of Food Science* 68(2): 539-544.

RF heating offers advantages of more uniform heating over the sample geometry due to both deeper level of power penetration and also simpler more uniform field patterns compared to MW heating. In contrast to RF-heating, higher frequency microwaves may provide for greater heating intensity, however, have limits for biomass products when they cannot penetrate deeply enough or provide uniform heating. Power penetration depth decreases with shorter wavelength that is, increasing frequencies. Penetration depths at radio frequencies are of the order of meters and, unless the loss factor is extremely high, through heating may be assured. In the microwave region, on the other hand, the penetration depths become very small, especially when a material is very wet. The wavelength at the RF heating frequencies designated by the Federal Communication Commission (FCC) for industrial heating is 22 to 360 times as great as that of the 2 commonly used microwave frequencies, which allows RF energy to penetrate dielectric materials more deeply than microwaves. Thus, radio frequency heating shows unexpected results in biomass treatment and dielectric materials processing at larger scales and higher levels of solids loading (e.g., about >20% w/w and about >70% w/w).

Over the past number of years, many studies have focused on rapid heating in solid and semi-solid foods using MW. The goal of much of this research was the achievement of rapid heating while attempting to evaluate the impact on the quality of the final product. One of the characteristics of MW heating is that it is limited by the relatively small penetration depth of MWs, which makes this technology profitable only for small sized foods. However, the use of RF can generally speaking, overcome this limitation. In fact, wavelength at the RF frequencies (e.g., 1 to 300 MHz) is up to 360 times greater than the wavelength corresponding to the two frequency values commonly used for MW (e.g., 915 MHz and 2.450 GHz). It allows RF energy to penetrate dielectric materials such as foods more deeply than MWs. Wang, et al. (2003) *Journal of Food Science* 68(2): 539-544.

In RF heating, a food product is placed in between two electrodes where an electromagnetic field is created by conversion of electric energy. Movement of positive ions to the negative regions and negative ions to the positive region (ionic depolarization) causes heating when electromagnetic field is applied at RF wavelengths. This mechanism is also valid in the MW heating in addition to the dipole rotation, which refers to the alignment of dipole molecules according to the polarity of the electromagnetic field. RF heating depends on the dielectric properties of the foods, which is influenced by frequency, temperature, moisture content and composition. Marra, et al. (2009) *Journal of Food Engineering* 91(4): 497-508; Piyasena, et al. (2003). Longer wavelengths of RF with respect to microwaves (MW) provide higher penetration depth, which allows heating of thicker products, like chicken breast meat. Overcooking is avoided while energy is transferred by longer wavelengths. However, the risks of arcing and thermal runaway are the main problems that limits the use of RF heating in the food industry (Zhao, Flugstad, Kolbe, Park, & Wells, 2000).

RF heating has been proven to allow rapid heat transfer throughout dielectric materials as the volumetric heating does not depend on heat transfer through the surface and continues through the boiling point of water and beyond. RF heating is a heating technology that allows for rapid, uniform heating throughout a medium. This technology generates greater energy within the product and throughout its mass simultaneously due to frictional interactions of polar dielectric molecules rotating to an applied external electric field. RF dielectric heating offers several advantages over conventional heating methods in food application, including saving energy by increasing heat efficiency, achieving rapid and even heating, reducing checking, avoiding pollution as there are no byproducts of combustion. Cathcart and Park (1946) first studied the use of RF heating to thaw frozen eggs, fruits, vegetables, and fish. Radio frequency dielectric heating is now widely used in industrial applications such as drying wood logs, textile products (e.g., spools, rovings, skeins), final drying of paper, final dehydration of biscuits at outlets of baking ovens, and melting honey (Barker 1983; Orfeuil 1987).

The problem however with a straight forward use of electromagnetic (EM) (e.g., radiofrequency) wave heating of biomass and ionic liquid complex is the generation of runaway temperatures. In typical uses described above, water absorbs the impinging energy and helps raise the temperature of the complex. As water evaporates, the electromagnetic (EM) (e.g., radiofrequency) waves pass through that part of the material without further energy dissipation. With ionic liquids or complexes containing ions, that do not evaporate or are not meant to evaporate, the setup needs to be much more specifically controlled. The control may include several sensors (e.g., thermocouples, nano-sensors, flow sensors, or other types of sensors) that relay the local conditions so the electromagnetic (EM) (e.g., radiofrequency) unit for that region can be appropriately controlled (e.g., turned on/off or set to a different frequency/power). This setup as such can be used in treatment, hydrolysis (e.g., acid hydrolysis or enzymatic hydrolysis or IL based or a combination there of) or other reaction environments, whenever the loading of biomass with respect to the other components in the complex is relatively high.

The heating for the treatment of the biomass may comprise two phases: (1) Initial Phase where RF energy is applied to rapidly heat the biomass and (2) Maintenance Phase where of ultrasonics, electromagnetic irradiation (EM) (e.g., radiofrequency), convective, conductive heating, or combinations thereof is applied to maintain the heat of the biomass.

The heating of the biomass by RF may be monitored by a microcontroller and maintained within set parameters of temperature and pressure. For example, the biomass may be maintained at a pre-determined temperature, and additional RF applied when the temperature of the biomass falls below this target temperate and RF is discontinued when the temperature of the biomass exceeds the target temperature. This process may be repeated to maintain an average temperature of the biomass during RF heating.

The inventors surprisingly found that the RF heating may rapidly, uniformly, and effectively heat the IL swelled biomass, biomass/IL slurry, or biomass/IL suspension allowing for a faster processing time of the biomass. Also, the use of RF heating unexpectedly allowed for higher solids loading (e.g., >30% w/w).

Radio frequency (RF) may comprise a frequency between at least about 3-30 Hz, 30-300 Hz, 300-3000 Hz, 3-30 kHz, 30-300 kHz, 300 kHz-3 MHz, 3-30 MHz, or 30-300 MHz. The radio frequency (RF) may be about 13, 13.56, 27, 27.12, 40, or 40.68 MHz.

The biomass may heated to a temperature of at least about 10° C., 20° C., 30° C., 40° C., 50° C., 60° C., 70° C., 80° C., 90° C., 100° C., 120° C., 130° C., 140° C., 150° C., 200° C., 300° C., 400° C., 60° C.-130° C., 80° C.-175° C., 130° C.-150° C., or 100° C.-240° C.

The radiofrequency may penetrate RF penetrates the biomass to about 0.001 to 2.0 meters thickness. The radiofrequency heating may occur with agitation, either intermittent or continuous.

The biomass may be heated with RF for at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 seconds. The biomass may be heated with RF for at least about 1-60 seconds, 1-30 seconds, 1-20 seconds, 5-10 seconds, or 1-10 seconds. The biomass may be heated with RF for at least about 10, 20, 30, 40, 50, 60 seconds. The biomass may be heated with RF for at least about 1, 2, 3, 4, 5, 6, 7, 8, 9, 10, 20, 30, 40, 50, 60, 70, 80, 90, 100, 110, 120, 130, 140, 150, 160, 170, or 180 minutes. The biomass may be heated with RF for at least about 1, 2, 3, 4, 5, 6, 7, 8, 9, 10, 11, 12, 13, 14, 15, 16, 17, 18, 19, 20, 21, 22, 23, or 24 hours. The biomass may be heated with RF for at least about 1, 2, 3, 4, 5, 6, 7, 8, 9, or 10 days. The biomass may be heated with RF for at least about 5-10 seconds, 10-30 seconds, 10-30 minutes, 1-30 minutes, 5-30 minutes, 1-20 minutes, 20 minutes to 2 hours, 5 minutes to 3 hours, 5 minutes to 2 hours, 1-4 hours, 2-4 hours, 1-2 hours, or 3-4 hours.

The biomass may treated at a pressure of at least about 1, 2, 3, 4, 5, 6, 7, 8, 9, 10, 11, 12, 13, 14, 15, 16, 17, 18, 19, 20, 30, 40, 50, 60, 70, 80, 90, or 100 atmospheres (atm).

The ultrasonics used in the methods described herein may be sound waves with high frequency about between 15-40 kHz, 20-30 kHz, 25-35 kHz, or about 15, 20, 30, 35, 35, or 40 kHz) with an amplitude between about amplitude about between 0.0001-0.025 mm. The ultrasonics heating may occur with agitation, either intermittent or continuous.

The biomass may be heated at a power of 100-1,000 W, 1 KW-10 KW, or 5 KW-1 MW.

The biomass may be comminuted to smaller sized particles. The biomass may be comminuted to smaller sized particles prior to mixing with an ionic liquid. The biomass may be comminuted to small particles about 0.1-20 mm, 0.1-2 mm, or about 5 mm in size.

The biomass may be processed at a high level of biomass. The biomass-ionic liquid slurry may comprise high solids loadings at least about 10%, 20%, 30%, 40%, 50%, 60%, 70%, 80%, 90%, or 95% w/w. The IL swelled biomass may comprise high solids loadings at least about 10%, 20%, 30%, 40%, 50%, 60%, 70%, 80%, 90%, or 95% w/w. The biomass may be loaded at high solids loading at approximately 30% w/w. The inventor surprisingly discovered that the use of electromagnetic heating (e.g., radiofrequency heating, variable frequency electromagnetic heating) allows for the treatment of biomass at high solids loading levels, e.g., >30% w/w.

A system and method for treatment of biomass may employ a variable frequency in the electromagnetic spectrum in combination with an ionic liquid. A system and method for treatment of biomass may employ a variable frequency in the electromagnetic spectrum in combination with an ionic liquid and an acid. The treated biomass may be further processed to yield renewable fuels, chemicals and materials, optionally ethanol, butanol, lactic acid, gasoline, biodiesel, methane, hydrogen, electricity, plastics, composites, protein, drugs, fertilizers or other components thereof.

The electromagnetic heating used in the methods and systems described herein may be a variable frequency in the electromagnetic spectrum (e.g., radiofrequency).

Ionic Liquid (IL)

The present invention is a new strategy for the treatment of lignocellulosic biomass by using radio frequency heating in conjunction with ionic liquids (ILs) to facilitate efficient and rapid enzymatic hydrolysis of its carbohydrates. Exemplary ionic liquids (IL) and treatment methods are described in U.S. Pat. No. 8,030,030.

Ionic liquids are liquids at room temperature and may contain only ions and are molten salts stable up to 300° C. See Sheldon (2001) *Chem. Commun.* 23: 2399-2407. They contain cations which are usually organic compounds and anions of inorganic or organic components such that the resulting salts are asymmetric. Because of poor packing associated with the asymmetric nature of ILs, crystal formation is inhibited and ILs remain liquids over a wide range of temperatures. A wide range of anions and cations can be employed to generate ILs with varied melting points, viscosities, thermal stabilities and polarities. Examples of some of the cations currently used include ammonium, sulfonium, phosphonium, lithium, imidazolium, pyridinium, picolinium, pyrrolidinium, thiazolium, triazolium oxazolium, or combinations thereof. Murugesan & Linhardt (2005) *Current Organic Synthesis* 2: 437-451. Ionic liquids are also liquid at <100° C., broad liquid range, almost no vapor pressure, high polarity, high dissolving power for organic and inorganic materials, good thermal, mechanical, and electrochemical stability, high heat capacity, non-flammable, and electrical conductivity.

Ionic liquids have extremely low volatility and when used as solvents, they do not contribute to emission of volatile components. In this sense they are environmentally benign solvents. ILs have been designed to dissolve cellulose and lignocellulose. Following dissolution, cellulose can be regenerated by the use of anti-solvents. However, the complete dissolution of lignocellulosic materials (particularly woods) in ILs is harder and, even partial dissolution, requires very long incubation of biomass in IL at elevated temperatures. Even then, a high yield of cellulose is not generally achieved after regeneration. Fort, et al. (2007) *Green. Chem.* 9: 63.

The present invention differs from the classic approach to the use of ionic liquids in that the aim is not to dissolve lignocellulose, but rather to contact it with the IL for times sufficient to mainly disrupt lignin sheathing and swell the remaining biomass structure significantly (at least 30%) but not dissolve the lignocellulose and further apply radio frequency heating. This combination treatment enables the subsequent enzymatic hydrolysis process to proceed in a relatively short period of time as well as give quantitative yields of glucose and high yields of pentose sugars. Any ionic liquid capable of disrupting the hydrogen bonding structure to reduce the crystallinity of cellulose in the biomass can be used in the treatment methods described herein may comprise a cation structure that includes imidazolium, pyrroldinium, pyridinium, phosphonium, ammonium, or a combination thereof and all functionalized analogs thereof. For example, the structure of triazolium as shown in FIG. 4 wherein each of R1, R2, R3, R4, and R5 may be hydrogen, an alkyl group having 1 to 15 carbon atoms or an alkene group having 2 to 10 carbon atoms, wherein the alkyl group may be substituted with sulfone, sulfoxide, thioether, ether, amide, hydroxyl, or amine and wherein A may be a halide, hydroxide, formate, acetate, propionate, butyrate, any functionalized mono- or di-carboxylic acid having up to a total of 10 carbon atoms, succinate, lactate, aspartate, oxalate, trichloroacetate, trifluoroacetate, dicyanamide, or carboxylate. Another example of the structure of IL is shown in FIG. 4 pyridine wherein each of R1, R2, R3, R4, R5, and R6 may be hydrogen, an alkyl group having 1 to 15 carbon atoms or an alkene group having 2 to 10 carbon atoms, wherein the alkyl group may be substituted with sulfone, sulfoxide, thioether, ether, amide, hydroxyl, or amine and wherein A may be a halide, hydroxide, formate, acetate, propanoate, butyrate, any functionalized mono- or di-carboxylic acid having up to a total of 10 carbon atoms, succinate, lactate, aspartate, oxalate, trichloroacetate, trifluoroacetate, dicyanamide, or carboxylate. The halide can be a chloride, fluoride, bromide or iodide.

Also an ionic liquid mixture with a composition described by Equation 1 may be used in the methods and systems described herein.

$$\sum_{n=1}^{20} [C^+]_n [A^-]_n$$

$C^+$ denotes the cation of the IL and $A^-$ denotes the anionic component of the IL In Equation 1. Each additional IL added to the mixture may have either the same cation as a previous component or the same anion as a previous component, of differ from the first only in the unique combination of the cation and anion. For example, consider below the five component mixture of ILs in which common cations and anions are used, but each individual IL component is different: $[BMIM^+][Cl^-]+[BMIM^+][PF_6^-]+[EMIM^+][Cl^-]+[EMIM^+][PF_6^-]+[EMIM^+][BF_4^-]$ The final mixture of ionic liquids will vary in the absolute composition as can be defined by the mole percent of various functionalized cations and anions. Therefore, the mixture may be comprised of varying weight percentages of each utilized component, as defined by Equation 1. The use of several such representative solvents for treating biomass may be 1-Ethyl-3-Methylimidazolium Propionate (EMIM-Pr) as described in U.S. Pat. No. 8,030,030. Also the ionic liquid 1-(4-sulfonic acid) butyl-3-methylimidazolium hydrogen sulfate may be used.

The ionic liquid may have a water content not exceeding about 1, 2, 3, 4, 5, 6, 7, 8, 9, 10, 11, 12, 13, 14, 15, 16, 17, 18, 19, 20, 21, 22, 23, 24, or 25%. Also, the ionic liquid may be recovered and reused.

The biomass may be dissolved in an ionic liquid. The biomass may be dissolved in an ionic liquid and regenerated by use of an antisolvent. The antisolvent may be water, ethanol, methanol, acetone, or a mixture thereof.

Recovery of IL/Dehydration of IL

The wash effluent may be collected and the ionic liquid dehydrated by the application of RF energy. The RF energy heats IL faster than it heats water because of a stronger dipole moment in IL. Without being bound to a specific theory, the inventors surprisingly discovered that the ions try to align with the electromagnetic (EM) (e.g., radiofrequency) waves, always changing a dipole moment. The IL heated by RF acts as a substrate for the water to heat and evaporate from the IL wash effluent. Thus, the wash effluent comprising a solvent and ionic liquid may be heated using RF energy. The RF energy drive off the water which may be collected and removed from the wash. The resultant ionic liquid is thus dehydrated (e.g., the water has been removed) and may be reused.

Acidolysis

In an acidolysis treatment, the biomass is mixed with ionic liquid (IL), acid (e.g., sulfuric acid, hydrochloric acid, nitric acid, or phosphoric acid), and heated using electromagnetic energy, comprising two phases. In the first Initial Phase, radio frequency (RF) energy is used to heat the biomass. In the second, Maintenance Phase, of ultrasonics, electromagnetic irradiation (EM) (e.g., radiofrequency), convective, conductive heating, or combinations thereof is used to maintain the heat at a target temperature (e.g., 50-70° C.). Both the mixing with ionic liquid and heating steps may be monitored for sufficient penetration and uniform heating and the conditions (e.g., time, pressure, heat, intensity of RF energy) may be adjusted as necessary to maintain sufficient penetration and uniform heating of the biomass. Following acidolysis, the wash effluent may be collected and the ionic liquid dehydrated by the application of RF energy. Further, a base (e.g., NaOH, KOH) may be added to neutralize the biomass/IL slurry. Further, a base (e.g., NaOH, KOH) may be added to neutralize the IL swelled biomass. Also, the acidolysis may comprise agitation, either intermittent or continuous. After the acidolysis process, the sugars may then be separated from residual materials (e.g., lignin). The sugar solution may then be converted to chemicals (e.g., ethanol, lactic acid, succinic acid). The lignin may be recovered. Additionally, the acid may be recovered. The treatment of biomass with ionic liquid and acid including the application of electromagnetic (EM) (e.g., radiofrequency) heating may yield degradation products of the biomass including but not limited to 5-hydroxymethylfurfural, furan-2-carboxylic acid, catechol, methycatechol, methylguaiacol, acetoguaiacone, and acetol, as well as degradation of lignin for lignocellulosic biomass. See also Li, et al. (2010) *Ind. Eng. Chem. Res.* 49(7): 3126-3136.

For example, the biomass may be incubated with an ionic liquid (e.g., 1-allyl-3-methylimidazolium chloride) and 5% sulfuric acid or 5% hydrochloric and heated to 90° C. for 1-3 hours, 2 hours, 5-30 minutes, 1-30 minutes, or 5-15 minutes.

The acid may be added to the biomass ionic liquid slurry to achieve a pH of at least about 1, 2, 3, 4, 5, 6, 6.1, 6.2, 6.3, 6.4, 6.5, 6.6, 6.7, 6.8, or 6.9. The acid may be added to the biomass ionic liquid slurry to achieve a pH of at least about between 1-3, 2-4, 3-5, 4-6, or 5-6.5.

The acid may be added to the IL swelled biomass to achieve a pH of at least about 1, 2, 3, 4, 5, 6, 6.1, 6.2, 6.3, 6.4, 6.5, 6.6, 6.7, 6.8, or 6.9. The acid may be added to the IL swelled biomass to achieve a pH of at least about between 1-3, 2-4, 3-5, 4-6, or 5-6.5.

The acid may be at least about 1, 2, 3, 4, 5, or 6 M sulfuric acid, hydrochloric acid, nitric acid, or phosphoric acid. The acid may be at least about between 1-3, 2-4, 3-5, 4-6, or 5-6.5 M sulfuric acid, hydrochloric acid, nitric acid, or phosphoric acid.

The acidolysis reaction may be run at least about 50-70° C., 60° C., 80° C., 90° C., 100° C., 105° C., or 110° C.

Conversion to Value Added Products

The following processes may be used to convert biomass (e.g., cellulose, hemicellulose, and lignin) to value added chemicals (e.g., ethanol). See Corma, et al. (2007) "Chemical Routes for the Transformation of Biomass into Chemicals." *Chem. Rev.* 107: 2411-2502. The methods described herein separates the biomass into its main constituents:cellulose, hemicellulose, and lignin. The cellulose and hemicellulose may then be converted (e.g., hydrolysis) to sugars. For example, the hemicellulose may be converted to five and six carbon sugars (e.g., xylose, arabinose) and the cellulose may be converted to six-carbon sugars (e.g., glucose.) The sugars may then be fermented to product products (e.g., ethanol). The lignin may be converted to energy, fuel, plastics, or binders. The cellulose and hemicellulose may undergo a hydrolysis process (cellulolysis), either chemical treatment (e.g., acids) or a biochemical treatment (e.g., enzymatic digestion). Some methods for the chemical processing of cellulose, lignocellulose, and other biomass into chemicals are known in the art. See, e.g., Kobayashi, et al. (2012) *Catal. Sci. Technol.* 2: 869-883; Ishikawa & Saka (2001) "Chemical Conversion of Cellulose as treated in supercritical methanol." *Cellulose* 8(3): 189-195; Tao, et al. (2011) "Catalytic Conversion of cellulose to chemicals in ionic liquid." *Carbohydrate Research* 346(1): 58-63; Tao, et al. (2011) *Carbohydrate Research* 346(1): 58-63; and Binder & Raines (2009) *J. Am. Chem. Soc.* 131: 1979-1985. These methods may be used in conjunction with the treatment and treatment methods described herein.

Chemical Conversion to Value Added Products

The chemical treatment may comprise incubation with acids under heat and pressure or a concentrated acid hydrolysis process (e.g., Scholler process). See also Robinson (1995) "A Mild, Chemical Conversion of Cellulose to Hexane and Other Liquid Hydrocarbon Fuels and Additives," *ACS Fuel Chemistry Preprints* 40(3): 729 and Binder & Raines (2010) *PNAS* 107(10): 4516-4521. The cellulose may be treated with alkaline peroxide and then treated with enzymes to break down the cell wall. For example, the biomass may be treated with an ionic liquid to convert the sugars (e.g., glucose and fructose) into 5-hydroxymethylfurfural (HMF). Oxidation of HMF yields 2,5-furandicarboxylic acid.

In other processes, the cellulose and hemicellulose may be converted to 5-hydroxymethylfurfural (HMF) that may be used as a raw material for plastics and fuels. A metal chloride (e.g., chromium chloride) may be used with an ionic liquid to convert the sugars (e.g., glucose and fructose) into HMF. The chemical, a metal chloride known as chromium chloride, converted sugar into highly pure HMF. The metal chlorides and ionic liquid may be resused. Oxidation of HMF yields 2,5-furandicarboxylic acid, which may be used as a replacement for terephthalic acid in the production of polyesters (e.g., polyethylene terephthalate (PET)). See Zhao, et al. (2007) *Science* 316(5831): 1597-1600.

Further, the cellulose may be degraded by the use of cooperative ionic liquid pairs for combined dissolution and catalytic degradation of cellulose into 2-(diethoxymethyl)furan. See Long, et al. (2011) *Green Chem.* 13: 2334-2338.

Catalysts may be used in the methods described herein to increase the reaction rate of the reactions. For example, alkali and alkaline earth metal chlorides, and transition metal chlorides (e.g., $CrCl_3$, $FeCl_2$, and $CuCl_2$), and IIIA metal chlorides (e.g., $AlCl_3$) may be used as catalysts. See, e.g., Peng, et al. (2010) *Molecules* 15: 5258-5272. Additionally, $CoSO_4$ may be used as a catalyst in conjunction with an ionic liquid.

Additionally, the sugars produced by the methods described herein may be used to produce succinic acid, glycerol, 3-hydropropoionic acid, 2,5-dimethylfuran (DMF), 5-hydroxymethyl furfural (HMF), furfural, 2,5-furandicarboxylic acid, itaconic acid, levulinic acid, aldehydes, alcohols, amines, terephthalic acid, hexamethylenediamine, isoprene, polyhydroxyalkanoates, 1,3-propanediol, or mixtures thereof.

Also, the treated biomass produced by the methods described herein may be used to produce succinic acid, glycerol, 3-hydropropoionic acid, 2,5-dimethylfuran (DMF), 5-hydroxymethyl furfural (HMF), furfural, 2,5-furandicarboxylic acid, itaconic acid, levulinic acid, aldehydes, alcohols, amines, terephthalic acid, hexamethylenediamine, isoprene, polyhydroxyalkanoates, 1,3-propanediol, or mixtures thereof. Also, the chemical processing of the treated biomass may yield gas productions including but not limited to methane, ethane, CO, $CO_2$, and $H_2$.

Biochemical Conversion to Value Added Products

In enzymatic hydrolysis, the cellulose is digested into sugar molecules by cellulase enzymes. The lignocellulosic materials may be enzymatically hydrolyzed at mild conditions (e.g., 50° C. and pH 5) to breakdown the cellulose. For example, cellobiohydrolase, exo-1,4-β-glucanase, do-beta-1, 4-glucanase, beta-glucosidase, endocellulase, exocellulase, cellobiase, and beta-1,4-glucanase may be used for enzymatic digestion of cellulose. The hemicellulases include but are not limited to laminarinase, lichenase, β-xylosidase, xylanases (e.g., endo-1,4-β-xylanase, xylan 1,4-β-xylosidase, xylan endo-1,3-β-xylosidase, xylan 1,3-β-xylosidase), α-L-arabinofuranosidase, arabianan endo-1,5-α-L-arabinosidase, mannananses (e.g., mannan endo-1,4-β-mannosidase, mannan 1,4-β-mannosidase, mannan 1,4-β-mannobisosidase, mannan endo-1,6-β-mannosidase), galactanases, and xylanase may be used for enzymatic digestion of hemicellulase. Jeffries "8. Biodegradation of lignin and hemicelluloses." *Biochemistry of Microbial Degradation* pages 233-277. The cellulase, xylanase, and hemicellulase enzymes may be recombinant, including those expressed by recombinant fungi. See Lynd (1996) *Annu Rev Energy Environ* 21: 403-465.

In the enzymatic treatment of the treated biomass, the biomass may be heated to at least about 50-100° C., 55° C., or 70° C.

In the combined hydrolysis and fermentation approach, the cellulose and hemicellulose may be incubated with *Clostridium thermocellum* which uses its a complex cellulosome to break down cellulose into ethanol, acetate, and lactate.

For ethanol production, the cellulose may undergo cellulolysis processes or gasification. In cellulolysis, the treated lignocellulosic biomass undergoes hydrolysis and then the cellulose may be treated by microbial fermentation. For example, the cellulose may be incubated with *Saccharomyces cerevisiae, Zymomonas mobilis*, and *Escherichia coli*, including recombinant microbes, to ferment xylose and arabinose to produce sugars and ethanol. See Jeffries & Jin (2004) *Appl Microbiol Biotechnol* 63(5): 495-509. The gasification process, a thermochemical approach, the cellulose and hemicellulose is converted into synthesis gas. The carbon monoxide, carbon dioxide and hydrogen may then be incubated with *Clostridium ljungdahlii*. The *Clostridium ljungdahlii* ingests carbon monoxide, carbon dioxide, and hydrogen to produce ethanol and water.

Thermostable enzymes may be used in the hydrolysis step. Thermostable enzymes may be stable and active up to about 70° C., as opposed to 55° C. for most commercially available enzymes.

Additionally, the sugars produced by the methods described herein may be used to produce succinic acid, glycerol, 3-hydropropoionic acid, 2,5-dimethylfuran (DMF), 5-hydroxymethyl furfural (HMF), furfural, 2,5-furandicarboxylic acid, itaconic acid, levulinic acid, aldehydes, alcohols, amines, terephthalic acid, hexamethylenediamine, isoprene, polyhydroxyalkanoates, 1,3-propanediol, or mixtures thereof.

Also, the treated biomass produced by the methods described herein may be used to produce succinic acid, glycerol, 3-hydropropoionic acid, 2,5-dimethylfuran (DMF), 5-hydroxymethyl furfural (HMF), furfural, 2,5-furandicarboxylic acid, itaconic acid, levulinic acid, aldehydes, alcohols, amines, terephthalic acid, hexamethylenediamine, isoprene, polyhydroxyalkanoates, 1,3-propanediol, or mixtures thereof. Also, the biochemical processing of the treated biomass may yield gas productions including but not limited to methane, ethane, CO, $CO_2$, and $H_2$.

Further, the hemicellulose may be converted to xylose and then to ethanol, xylitol, plastics. The lignin may be converted to fuel, plastics, and binders. The cellulose may be converted to glucose and pulps.

Proceeding now to a description of the drawings, FIG. 1A shows an exemplary series for carrying out steps of a method of the present invention.

One of the following representative ionic liquids 1-n-butyl-3-methylimidazolium chloride (BMIMCl)/1-n-ethyl-3-methyl imidazolium acetate (EMIMAc)/1-ethyl-3-methyl imidazolium propionate (EMIMPr)/1-allyl-3-methyl imidazolium chloride/3-methyl-N-butylpyridinium chloride may be contacted with small particles of biomass 100 (e.g., dry corn stover or poplar (−20+80 mesh sized particles)] for varying times (about 5 minutes to 8 hours) 200. Incubation with biomass may be carried out using electromagnetic (EM) (e.g., radiofrequency) heating and ultrasonics, electromagnetic (EM) (e.g., radiofrequency), convective, conductive heating, or combinations thereof at about 50° C. to 200° C. as long as the ionic liquid is in molten state during incubation 300. The conditions may be monitored by use of sensors and adjusted to maintain conditions. The biomass may be heated with RF heating at about 27 mHz for at least about 5 seconds to 2 hours. The IL swelled biomass may then be heated using ultrasonics, electromagnetic (EM) (e.g., radiofrequency), convective, conductive heating, or combinations thereof is for about at least 3-30 minutes or 3-4 hours. The conditions may be monitored and adjusted to maintain uniform heating and sufficient penetration of the biomass by the RF waves. Steps 200, 300, and/or 400 may be repeated. Further, steps 300 and/or 400 may be carried out in batch or continuous form. The goal of treatment 300 is not achieving any dissolution of lignocellulose, but heating the IL swelled biomass for sufficient time to redistribute lignin and swell the remaining biomass structure to enhance the hydrolysis rate and conversion of cellulose and hemicellulose to their constituent sugars 600.

The treated biomass may then contacted with one of the representative wash-solvents, namely, methanol/ethanol/water/acetonitrile/butanol/propanol 400. The wash-solvent mixes with the IL (in all proportions) and hence is able to extract it from the incubated biomass. The treated biomass may then be separated from the ionic liquid/wash solvent solution by centrifugation. The biomass, stripped off the IL, may then hydrolyzed with a cellulase system 500. The IL may be recovered from the wash-solvent and any dissolved biomass components from the wash-step through suitable separation methods including at least one of the following: activated charcoal treatment, distillation, membrane separation, electrochemical separation techniques, solid phase extraction, liquid-liquid extraction, or a combination thereof. The ionic liquid may then be recycled back to the treatment tank. The wash solvent also may be recycled back for reuse in washing IL-incubated biomass. The wash solvent may also be dehydrated by RF heating to dehydrate the wash solvent, driving off the water leaving a dehydrated IL.

The IL may be recovered from the IL/wash solvent mixtures by evaporation of the wash solvent (ethanol and/or water) from the extremely low volatility IL 400. The recovered IL may then be used with no additional cleaning steps in subsequent biomass treatment cycles at constant treatment conditions. The method allows for the repeated reuse of the IL with minimal cleaning which may lead to increased cost savings in IL-treatment.

Residual water in the recycled IL can lower the IL's capacity to sever the inter- and intra-chain hydrogen bonds imparting crystallinity to cellulose. In order to affect swelling of biomass, several of the cellulosic hydrogen-bonds have to be disrupted. Accordingly, it is expect dissolved water to affect IL's performance as a biomass treatment solvent. The admissible water content in IL can affect the economics of the treatment method in two aspects. First, it determines how dry the IL has to be before it can be reused. Second, it determines how dry the biomass has to be during incubation with IL.

After hydrolysis 500, enzymes may be recovered from the hydrolysis reactor and recycled. Complete removal of wash solvent (water) is not necessary before the IL is recycled. Many other treatment methods are not amenable to easy recovery of the chemicals employed in the process. Following hydrolysis (saccharification) with an appropriate enzyme mix, capable of converting all the carbohydrates in the pretreated biomass to sugars, most of the solids left behind in the saccharification reactor represent the lignin portion of the biomass. This provides a method of recovering the lignin from biomass 700. Also, ultra-filtration of the liquid portion of the hydrolysate, provides a means of recovering the hydrolysis enzymes for reuse from the sugar solution which is the precursor for the production of a number of fuels and chemicals 700.

The current method of treatment with RF and ionic liquid, optionally, followed by hydrolysis (saccharification technique) 500 allows for recovering the lignin in the biomass 700 in the form a post saccharification solid residue. Finally, the sugars in the hydrolysate obtained following treatment of biomass 300 may be converted 600 to fuel ethanol or other bioproducts such as lactic acid with no further conditioning and adverse effects from any residual traces of IL in the hydrolysate. Further chemical/biochemical processing of this residue may lead to compounds which could be used for the production of fuels, chemicals, polymers and other materials.

FIG. 1B shows an exemplary series for carrying out steps of a method of the present invention.

One of the following representative ionic liquids 1-n-butyl-3-methylimidazolium chloride (BMIMCl)/1-n-ethyl-3-methyl imidazolium acetate (EMIMAc)/1-ethyl-3-methyl imidazolium propionate (EMIMPr)/1-allyl-3-methyl imidazolium chloride/3-methyl-N-butylpyridinium chloride may be contacted with small particles of biomass 101 (e.g., dry corn stover or poplar (−20+80 mesh sized particles)] for varying times (about 5 minutes to 8 hours) to the swell the biomass with the IL 201. Heating of the IL swelled biomass may be carried out by first electromagnetic (EM) (e.g., radiofrequency) heating to reach a target temperature or temperature range (e.g., 50° C.-220° C.) 301 and then heating using ultrasonics, electromagnetic (EM) (e.g., radiofrequency), convective, conductive heating, or combinations thereof at about 50° C. to 200° C. for 3-30 minutes or 3-4 hours 302. The conditions may be monitored by use of sensors and adjusted to maintain conditions 301 302. The conditions may be monitored and adjusted to maintain uniform heating and sufficient penetration of the biomass by the RF waves. Steps 201, 301, 302, and/or 401 may be repeated. Further, steps 301, 302, and/or 401 may be carried out in batch or continuous form.

The treated biomass may then contacted with one of the representative wash-solvents, namely, methanol/ethanol/water/acetonitrile/butanol/propanol 401. The wash-solvent mixes with the IL (in all proportions) and hence is able to extract it from the incubated biomass. The treated biomass may then be separated from the ionic liquid/wash solvent solution by centrifugation. The biomass, stripped off the IL, may then hydrolyzed with a cellulase system 501. The IL may be recovered from the wash-solvent and any dissolved biomass components from the wash-step through suitable separation methods including at least one of the following: activated charcoal treatment, distillation, membrane separation, electrochemical separation techniques, solid phase extraction, liquid-liquid extraction, or a combination thereof. The ionic liquid may then be recycled back to the treatment tank. The wash solvent also may be recycled back for reuse in washing IL-incubated biomass. The wash solvent may also be dehydrated by RF heating to dehydrate the wash solvent, driving off the water leaving a dehydrated IL 701.

The IL may be recovered from the IL/wash solvent mixtures by evaporation of the wash solvent (ethanol and/or water) from the extremely low volatility IL 400. The recovered IL may then be used with no additional cleaning steps in subsequent biomass treatment cycles at constant treatment conditions. The method allows for the repeated reuse of the IL with minimal cleaning which may lead to increased cost savings in IL-treatment.

After hydrolysis 501, enzymes may be recovered from the hydrolysis reactor and recycled. Complete removal of wash solvent (water) is not necessary before the IL is recycled. Many other treatment methods are not amenable to easy recovery of the chemicals employed in the process. Following hydrolysis (saccharification) with an appropriate enzyme mix, capable of converting all the carbohydrates in the pretreated biomass to sugars, most of the solids left behind in the saccharification reactor represent the lignin portion of the biomass. This provides a method of recovering the lignin from biomass 700. Also, ultra-filtration of the liquid portion of the hydrolysate, provides a means of recovering the hydrolysis enzymes for reuse from the sugar solution which is the precursor for the production of a number of fuels and chemicals 700.

The current method of treatment with RF and ionic liquid, optionally, followed by hydrolysis (saccharification technique) 500 allows for recovering the lignin in the biomass 700 in the form a post saccharification solid residue. Finally, the sugars in the hydrolysate obtained following treatment of biomass 301 302 may be converted 600 to fuel ethanol or other bioproducts such as lactic acid with no further conditioning and adverse effects from any residual traces of IL in the hydrolysate. Further chemical/biochemical processing of this residue may lead to compounds which could be used for the production of fuels, chemicals, polymers and other materials.

FIG. 1C shows an exemplary series for carrying out steps of a method of the present invention.

Biomass 102 may be mixed with an ionic liquid (e.g., 1-allyl-3-methylimidazolium chloride) for varying times (e.g., about 5 minutes to 8 hours) to swell the biomass 202. An acid, optionally sulfuric acid, hydrochloric acid, nitric acid, or phosphoric acid, may be added to the IL swelled biomass to achieve an acidic pH, optionally a pH of about 1, 2, 3, 4, 5 or 6, or below pH 7, and then heated 800. Heating of the IL swelled biomass may be carried out by first electromagnetic (EM) (e.g., radiofrequency) heating to reach a target temperature or temperature range (e.g., 50° C.-220° C.) and then heating using ultrasonics, electromagnetic (EM) (e.g., radiofrequency), convective, conductive heating, or combinations thereof at about 50° C. to 200° C. (e.g., 120° C.) for 3-30 minutes or 3-4 hours. The conditions may be monitored by use of sensors and adjusted to maintain conditions. The conditions may be monitored and adjusted to maintain uniform heating and sufficient penetration of the biomass by the RF waves. Steps 102, 202, and/or 800 may be repeated. Further, steps 102, 202, and/or 800 may be carried out in batch or continuous form. Further, a base (e.g., NaOH, KOH) may be added to neutralize the IL swelled biomass after the acidolysis treatment.

The ionic liquids may also be dehydrated by RF heating to dehydrate the wash solvent, driving off the water leaving a dehydrated IL 702.

After acidolysis 800, the sugars may be converted 600 to fuel ethanol or other bioproducts such as lactic acid. Additionally, the residual solids (e.g. lignin) may be converted to other product 700. Further chemical/biochemical processing of this residue may lead to compounds which could be used for the production of fuels, chemicals, polymers and other materials.

FIG. 1D shows an exemplary series for carrying out steps of a method of the present invention.

The biomass 103 may be mixed with an ionic liquid 203 and the biomass may be dissolved in the ionic liquid 204. Heating of the biomass/IL solution may be carried out by first electromagnetic (EM) (e.g., radiofrequency) heating 303 to reach a target temperature or temperature range (e.g., 50° C.-220° C.) and then heating using ultrasonics, electromagnetic (EM) (e.g., radiofrequency), convective, conductive heating, or combinations thereof 304 at about 50° C. to 200° C. (e.g., 120° C., 130° C., 140° C., 150° C.) for 1-180 minutes or 3-4 hours. The conditions may be monitored by use of sensors and adjusted to maintain conditions. The conditions may be monitored and adjusted to maintain uniform heating and sufficient penetration of the biomass by the RF waves. The biomass may be regenerated using an antisolvent, optionally water, ethanol, methanol, acetone, or mixtures thereof 205. The regenerated biomass may be washed 205. The IL may be recovered and reused 703. The regenerated biomass may undergo hydrolysis (e.g., addition of cellulase and hemicellulases) of the cellulose and hemicellulose to their constituent monomeric sugars (e.g., five and six carbon sugars), optionally recovery of the added enzymes 502. The hydrolystate stream comprising sugars may be separated for further processing to produce chemicals or biofuels 600 and the residual solids comprising proteins and lignin 700 for further processing to produce chemicals or biofuels.

Apparatuses

FIG. 5 shows an exemplary apparatus and systems for carrying out steps of a method of the present invention.

FIG. 5A is a schematic diagram of a continuous belt press radiofrequency biomass processing system. In this embodiment, the biomass passes between a top and bottom electrode where the biomass is subject to radiofrequency heating. Fiber optic sensors in the biomass or the container monitor the heat of the biomass and penetration of the radiofrequency energy. The fiber optic sensors are coupled to a monitor system allows for the monitoring of the heat of the biomass and penetration of the radiofrequency energy which may be adjusted accordingly to maintain uniform heating and sufficient penetration of the biomass by the radiofrequency energy. In FIG. 5A, the biomass may be admixed with an ionic liquid in a container, then the container comprising the biomass admixed with an ionic liquid is moved into an apparatus comprising a top and bottom electrode that heats the biomass admixed with an ionic liquid with radiofrequency heating. An air distribution box allows for the further modulation of pressure and air temperature in the system. The method described herein may be a batch method, for example, the biomass may be mixed/slurried with ionic liquid and then transferred (e.g., via conveyer belt) to a second apparatus where it is heated with RF waves.

In FIG. 5B, the biomass 101 may be fed into a long conduit comprising an Archimedes screw to move the biomass along the conduit through three zones. In the first zone, the Mixing Zone the biomass is mixed with an ionic liquid to form a biomass/ionic liquid 201. The IL swelled biomass is then moved to a second zone where the IL swelled biomass is subjected to variable RF heating 301. The biomass following variable RF heating is washed 401, optionally recovering the ionic liquid for reuse. The method described herein may be a continuous method, for example, the biomass may be mixed/slurried with ionic liquid and then transferred to a second area where it is treated with RF waves.

Bioreactor

The invention also provides for a system for treating biomass comprising a reactor vessel coupled to a sensor network coupled to a feedback means for controlling the time, temperature, pressure, and water content of the interior of the reactor vessel.

Although certain manufacturers, model names and numbers are given for machinery used in the invention, other machinery may be substituted, as would be appreciated by those skilled in the art.

Although certain ranges are provided for the temperature, conveyor speed, electromagnetic (EM) (e.g., radiofrequency) wave intensity, and pressure characteristics, these can be varied based on the particular volumes desired, space requirements and other needs. After reading this specification, one skilled in the art will understand that the selection of working or optimum numbers for these variables may be made once the plant and overall process parameters of a particular processing installation are known.

Additionally, although preferred systems are disclosed for controlling the temperature of the IL swelled biomass, these may be varied. These may be varied by substituting, depending on normal plant considerations of energy cost, plant layout and the like, and generally the temperature values used in the process tolerate some ongoing variability due to, for instance, changes in ambient plant temperatures and other related factors.

All publications (e.g., Non-Patent Literature), patents, patent application publications, and patent applications mentioned in this specification are indicative of the level of skill of those skilled in the art to which this invention pertains. All such publications (e.g., Non-Patent Literature), patents, patent application publications, and patent applications are herein incorporated by reference to the same extent as if each individual publication, patent, patent application publication, or patent application was specifically and individually indicated to be incorporated by reference.

Although methods and materials similar or equivalent to those described herein may be used in the invention or testing of the present invention, suitable methods and materials are described herein. The materials, methods and examples are illustrative only, and are not intended to be limiting.

The invention now being generally described, it will be more readily understood by reference to the following examples, which are included merely for purposes of illustration of certain aspects and embodiments of the present invention, and are not intended to limit the invention.

EXAMPLES

Example 1

Method for Processing Feedstock

A method for processing biomass comprises contacting feedstock with ionic liquids to form a uniform solution (suspension) and transferring (e.g., injecting) it into a closed variable electromagnetic (EM) wave device. With the application of RF, the temperature in the biomass will be monitored and the RF frequency will be varied to adjust for achieving uniform temperature distribution within the RF device biomass processing unit.

The biomass treating method disclosed herein heat the biomass/products with ions which gets heated due to dipole movement because of RF application (e.g., 27 MHz) continuously. This generates rapid uniform volumetric heating within the entire product due to frictional interaction between the molecules due to dipole heating of ions. Although identical to the microwave in terms of its heating characteristics, radio frequency has the added advantage of uniform, and most important of all, high penetration Depth that could be used to pasteurize or sterilize liquid products. For RF heating, penetration depth is generally greater than 1 m, and can be determined from a relationship that embodies the dielectric constant, the loss factor, the speed of wave propagation in vacuum, and, operating frequency (Orfeuil, 1987). Depending on concentration of biomass, ionic liquids and their ratios, and temperature, the penetration depth of biomass can vary from 0.2 to 2.1 m in the radio frequency range.

Preferred embodiments of apparatus schematics for carrying out processing biomass with ionic liquids using RF device may seen in FIGS. 2 and 5.

Those skilled in the art will recognize, or be able to ascertain using no more than routine experimentation, many equivalents to the specific embodiments of the invention described herein. Such equivalents are intended to be encompassed by the following claims.

We claim:

1. A method for the treatment of biomass comprising mixing a biomass with an ionic liquid (IL) to swell said biomass and radiofrequency (RF) heating said swelled biomass, wherein said heating comprises at least two phases, a first phase comprising heating and a second phase comprising application of radiofrequency (RF) heating.

2. The method of claim 1, wherein said biomass is agricultural residues; wood and forest residues; algae; kudzu; coal; cellulose, lignin, herbaceous energy crops; lignocellulosic; biomass; plant biomass; or mixtures thereof.

3. The method of claim 2, wherein said agricultural residues are corn stover, wheat straw, bagasse, rice hulls, rice straw, or combinations thereof.

4. The method of claim 2, wherein said wood and forest residues are pine, poplar, douglas fir, oak, saw dust, paper/pulp waste, wood fiber, or combinations thereof.

5. The method of claim 2, wherein said herbaceous energy crops are switchgrass, reed canary grass, miscanthus, or combinations thereof.

6. The method of claim 2, wherein lignocellulosic biomass comprises lignin, cellulose, and hemicellulose.

7. The method of claim 1, wherein said radiofrequency comprises a frequency between about 1-300 MHz, 3-30 kHz, 300 kHz-3 MHz, 3-30 MHz, 30-300 MHz, or 3 kHz to 3 MHz.

8. The method of claim 7, wherein said radiofrequency comprises a frequency between about 3-30 kHz.

9. The method of claim 1, wherein said biomass is heated in the first and second heating phase to a temperature of at least about 1-300° C., 50° C.-100° C., 60° C.-130° C., 80° C.-175° C., or 100° C.-240° C.

10. The method of claim 1, wherein said method further comprises washing the treated biomass.

11. The method of claim 10, wherein said washing comprises washing the biomass with a liquid non-solvent for cellulose that is miscible with water and the ionic liquid (IL).

12. The method of claim 11, wherein the liquid non-solvent used for washing is water, an alcohol, acetonitrile or a solvent which dissolves the IL and thereby extracts the IL from the biomass.

13. The method of claim 12, wherein said ionic liquid is recovered from the liquid non-solvent by activated charcoal treatment, distillation, membrane separation, electro-chemical separation techniques, solid-phase extraction, liquid-liquid extraction, or a combination thereof.

14. The method of claim 12, wherein said ionic liquid is recovered from the liquid non-solvent by application of electromagnetic heating, that dehydrates the ionic liquid.

15. The method of claim 14, wherein said electromagnetic heating is radiofrequency heating.

16. The method of claim 1, wherein the biomass is subjected to additional heating with agitation, ultrasonics heating, electromagnetic (EM) heating, convective heating, conductive heating, microwave irradiation, or a combination thereof.

17. The method of claim 16, wherein the biomass is subjected to additional heating, further comprising intermittent agitation during heating.

18. The method of claim 1, wherein the ionic liquid comprises a cation structure that includes ammonium, sulfonium, phosphonium, lithium, imidazolium, pyridinium, picolinium, pyrrolidinium, thiazolium, triazolium, oxazolium, or combinations thereof.

19. The method of claim 18, wherein the ionic liquid comprises a cation selected from imidazolium, pyrrolidinium, pyridinium, phosphonium, ammonium, or a combination thereof.

20. The method of claim 1, wherein the ionic liquid (IL) is 1-n-butyl-3-methylimidazolium chloride, 1-allyl-3-methyl imidazolium chloride, 3-methyl-N-butylpyridinium chloride, 1-ethyl-3-methyl imidazolium acetate, 1-ethyl-3-methyl imidazolium propionatem, or combinations thereof.

21. The method of claim 1, wherein the conditions of said biomass undergoing radiofrequency (RF) heating is monitored by means of sensors.

22. The method of claim 21, wherein said sensor is a liquid flow rate sensor, thermocouple sensor, temperature sensor, salinity sensor, or a combination thereof.

23. The method of claim 1, wherein said method further comprises treating said treated biomass with enzymes, to convert the cellulose and hemicellulose to sugars.

24. The method of claim 23, wherein said are thermophilic enzymes, that are active up to about 70° C.

25. The method of claim 23, wherein said method further comprises recovering the enzymes.

26. The method of claim 23, wherein said sugars are hexose sugars, pentose sugars, and mixtures thereof.

27. The method of claim 1, wherein said treatment produces a solid residue comprising proteins and lignin.

28. The method of claim 1, wherein said application of radiofrequency heating is for about 1-60 minutes.

29. The method of claim 1, wherein said biomass is heated in the first and second heating phase to a temperature of about 80° C.-175° C.

30. The method of claim 1, wherein said method is performed on a large scale.

31. The method of claim 1, wherein said method is performed with high solids loading.

32. The method of claim 31, wherein said high solids loading is >20% w/w.

33. The method of claim 1, wherein said first phase heating comprises convective heating, conductive heating, or a combination thereof.

34. The method of claim 1, wherein said method is a continuous method.

35. A method of acidolysis of biomass comprising
  (a) mixing biomass in an ionic liquid (IL) to swell said biomass;
  (b) adding an acid;
  (c) an initial heating phase comprising heating the biomass to heat to a target temperature range;
  (d) a maintenance heating phase comprising applying radiofrequency (RF) heating to the biomass to maintain the biomass at said target temperature range; and
  (e) recovering sugars.

36. The method of claim 35, wherein said method further comprises addition of a base to neutralize the pH of the biomass.

37. The method of claim 36, wherein the base is NaOH, KOH, or a combination thereof.

38. The method of claim 35, wherein said method further comprises washing said biomass after step (a).

39. The method of claim 35, wherein said acid is sulfuric acid, hydrochloric acid, nitric acid, or phosphoric acid.

40. The method of claim 35, wherein the method further comprises the step of lowering the pH of the biomass below pH 7.

41. The method of claim 40, wherein the pH is lowered to 1-6.

42. The method of claim 35, wherein the target temperature range is 50-220° C.

43. The method of claim 35, wherein said sugars are pentose, hexose, or a combination thereof.

44. The method of claim 35, wherein said initial phase heating comprises convective heating, conductive heating, or a combination thereof.

45. The method of claim 35, wherein said method is a continuous method.

* * * * *